United States Patent
Edgar et al.

(10) Patent No.: US 10,738,134 B2
(45) Date of Patent: Aug. 11, 2020

(54) CROSS-METATHESIZED POLYSACCHARIDE DERIVATIVES AND PROCESSES FOR PREPARING THEM

(71) Applicants: Kevin J. Edgar, Blacksburg, VA (US); Xiangtao Meng, Blacksburg, VA (US); John Matson, Blacksburg, VA (US)

(72) Inventors: Kevin J. Edgar, Blacksburg, VA (US); Xiangtao Meng, Blacksburg, VA (US); John Matson, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 235 days.

(21) Appl. No.: 15/025,451

(22) PCT Filed: Sep. 26, 2014

(86) PCT No.: PCT/US2014/057661
§ 371 (c)(1),
(2) Date: Mar. 28, 2016

(87) PCT Pub. No.: WO2015/048408
PCT Pub. Date: Apr. 2, 2015

(65) Prior Publication Data
US 2016/0215068 A1 Jul. 28, 2016

Related U.S. Application Data

(60) Provisional application No. 61/883,416, filed on Sep. 27, 2013.

(51) Int. Cl.
| | | |
|---|---|---|
| C08B 3/16 | (2006.01) | |
| C08B 3/00 | (2006.01) | |
| C08B 37/02 | (2006.01) | |
| C08B 37/00 | (2006.01) | |
| A61K 47/38 | (2006.01) | |
| C08B 3/14 | (2006.01) | |

(52) U.S. Cl.
CPC ............... *C08B 3/16* (2013.01); *A61K 47/38* (2013.01); *C08B 3/00* (2013.01); *C08B 3/14* (2013.01); *C08B 37/0018* (2013.01); *C08B 37/0021* (2013.01)

(58) Field of Classification Search
CPC ...................................................... C08B 3/16
USPC .................................................. 536/64, 65
See application file for complete search history.

(56) References Cited

U.S. PATENT DOCUMENTS

| | | | |
|---|---|---|---|
| 4,981,959 A | 1/1991 | Diamantoglou | |
| 2012/0178913 A1 | 7/2012 | Lin et al. | |
| 2012/0330002 A1 | 12/2012 | Cordova et al. | |
| 2013/0008830 A1 | 1/2013 | Ng et al. | |
| 2013/0248109 A1 | 9/2013 | Grubbs et al. | |

FOREIGN PATENT DOCUMENTS

| | | |
|---|---|---|
| WO | 2011156774 A2 | 12/2011 |
| WO | 2013106433 A1 | 7/2013 |

OTHER PUBLICATIONS

Chatterjee, A. K.; Choi, T. L.; Sanders, D. P.; Grubbs, R. H., A General Model for Selectivity in Olefin Cross Metathesis. J. Am. Chem. Soc. 2003, 125, (37), 11360-11370.

Choi, T. L.; Chatterjee, A, K.; Grubbs, R. H.; Synthesis of a βUnsaturated Amides by Olefin Crossmetathesis. Angew. Chem. Int. Ed. 2001,40, (7), 1277—+.

Co-pending Application PCT/US15/20726, International Search Report and Written Opinion, dated Jun. 10, 2015, 10 pages.

de Espinosa, L. M.; Kempe, K.; Schubert, U. S.; Hoogenboom, R.; Meier, M. A. R., Side-Chain Modification and "Grafting Onto" via Olefin Cross-Metathesis. Macrom. Rapid Comm. 2012, 33, (23), 2023-2028.

Grubbs, R. H., Olefin metathesis. Tetrahedron 2004, 60, (34), 7117-7140.

PCT/US2014/057661, International Search Report and the Written Opinion of the International Searching Authority, dated Dec. 29, 2014, 8 pages.

Joly, N.; Granet, R.; Krausz, P., Olefin Metathesis Applied to Cellulose Derivatives—Synthesis, Analysis, and Properties of New Crosslinked Cellulose Plastic Films. Journal of Polymer Science Part a—Polym. Chem. 2005,43, (2), 407-418.

Ilevbare, G. A.; Liu, H.; Edgar, K J.; Taylor, L. S., Impact of Polymers on Crystal Growth Rate of Structurally Diverse Compounds from Aqueous Solution. Mol. Pharm. 2013, 10, (6), 2381-2393.

Liu, H.; Ilevbare, G. A.; Cherniawski, B. P.; Ritchie, E. T.; Taylor, L. S.; Edgar, K. J., Synthesis and Structure-Property Evaluation of Cellulose w-Carboxyesters for Amorphous Solid Dispersions. Carbohydr. Polym., (2012), http://dx.doi.org/I0.I016/j.carbpoJ.2012.11.049.

Memmi, A.; Granet, R.; Gahbiche, M. A.; Fekih, A.; Bakhrouf, A.; Krausz, P., Fatty Esters of Cellulose from Olive Pomace and Barley Bran: Improved Mechanical Properties by Metathesis Crosslinking. J. Appl. Polym. Sci. 2006, 101, (1), 751-755.

(Continued)

*Primary Examiner* — Patrick T Lewis
(74) *Attorney, Agent, or Firm* — New River Valley IP Law, P.C.; Michele L. Mayberry

(57) ABSTRACT

Methods for the cross-metathesis of polysaccharides with one or more olefin-terminated side chains and cross-metathesized products are described. In an exemplary embodiment, a method for the synthesis of cellulose ω-carboxyesters via olefin cross-metathesis is described. Conditions of the reactions were relatively mild and the olefin-substituted polysaccharides and the appropriate monomeric olefin partners appear to follow Grubbs rules as summarized herein. The compounds and methods may be useful for structure-property studies, particularly those aimed at developing polymers for drug delivery, such as for controlled-release drug delivery systems, controlled-release coatings, increasing bioavailability of drugs, and maintaining drug supersaturation in the GI tract.

20 Claims, 7 Drawing Sheets

(56) References Cited

OTHER PUBLICATIONS

Meng et al. 'Olefin Cross-Metathesis as a Source of Polysaccharide Derivatives: Cellulose w-Carboxyalkanoates', Biomacromolecules 2014, vol. 15, pp. 177-187 (Published Dec. 13, 2013).
Meng et al., "Olefin cross-metathesis, a mild, modular approach to functionalized cellulose esters", Polymer Chemistry 5(4): 7021-7033, 2014.
Miao, X.; Fischmeister, c.; Dixneuf, P. H.;Bruneau, c.; Dubois, J. L; Couturier, J. L., Polyamide Precursors from Renewable 10-Undecenenitrile and Methyl Acrylate via Olefin Cross-metathesis. Green Chem. 2012, 14, (8), 2179-2183.
Miyata, O.; Shinada, T.; Ninomiya, I.; Naito, T.; Date, T.; Okamura, K; Inagaki, S., Stereospecific nucleophilic addition reactions to olefins. Addition of Thiols to α, β-Unsaturated Carboxylic Acid Derivatives. J.Org. Chem. 1991,56, (23), 6556-6564.
Mori, A.; Miyakawa, Y.; Ohashi, E.; Haga, T.; Maegawa, T.; Sajiki, H., Pd/C-catalyzed chemoselective hydrogenation in the presence of diphenylsulfide. Org. Lett. 2006, 8, (15), 3279-3281.
Reddy, C. R.; Jithender, E.; Prasad, K. R, Total Syntheses of the Proposed Structure for leodoglucomides A and B. J. Org. Chem. 2013, 78, (9), 4251-4260.
Rybak, A.; Meier, M. A. R., Cross-metathesis of Fatty Acid Derivatives with Methyl Acrylate: Renewable Raw Materials for the Chemical Industry. Green Chem. 2007, 9, (12), 1356-1361.
Samojlowicz, C.; Bieniek, M.; Grela, K., Ruthenium-Based Olefin Metathesis Catalysts Bearing NHeterocyclic Carbene Ligands. Chem. Rev. 2009,109, (8), 3708-3742.
Vougioukaiakis, "Removing Ruthenium Residues from Olefin Metathesis Reaction Products", Chem. Eur. J. 18: 8868-8880, 2012.
Vougioukalakis, G.C.; Grubbs, R. H., Synthesis and Activity of Ruthenium Olefin Metathesis Catalysts Coordinated with Thiazol-2-ylidene Ligands. J. Am. Chem. Soc. 2008, 130, (7), 2234-2245.
Zerkowski, J. A.; Solaiman, D. K. Y., Omega-Functionalized Fatty Acids, Alcohols, and Ethers via Olefin Metathesis. J. Am. Oil Chem. Soc. 2012, 89, (7), 1325-1332.
Co-pending U.S. Appl. No. 15/125,787, filed Sep. 13, 2016, published as U.S. Patent Application Publication No. 20160376379 on Dec. 29, 2018.
Co-pending U.S. Appl. No. 15/125,787, Non-Final Office Action dated Sep. 25, 2018, 7 pages.
Co-pending U.S. Appl. No. 15/125,787, Response to Jan. 2, 2018 Restriction Requirement dated Jul. 2, 2018. 3 pages.
Co-pending U.S. Appl. No. 15/125,787, Restriction Requirement dated Jan. 2, 2018, 8 pages.
Edgar, K.J. Direct synthesis of partially substituted cellulose esters, pp. 213-229, ACS Symposium Series No. 1017, 2009, K.J. Edgar, T. Heinze, C.M. Buchanan editors, American Chemical Society, Washington, D.C.
Meng, X.; Edgar, K.J. Synthesis of amide-functionalized cellulose esters by olefin cross-metathesis. Carbohydrate Polymers 2015, 132, 565-573.
Ilevbare, G. A.; Liu, H.; Edgar, K J.; Taylor, L. S., Effect of Binary Additive Combinations on Solution Crystal Growth of the Poorly Water-Soluble Drug, Ritonavir. Cryst. Growth Des. 2012, 12, (12), 6050-6060.
Ilevbare, G. A.; Liu, H.; Edgar, K J.; Taylor, L. S., Maintaining Supersaturation in Aqueous Drug Solutions: Impact of Different Polymers on Induction Times. Cryst. Growth Des. 2013, 13, (2), 740-751.
Ilevbare, G. A.; Liu, H.; Edgar, K. J.; Taylor, L. S., Understanding Polymer Properties Important for Crystal Growth Inhibition-Impact of Chemically Diverse Polymers on Solution Crystal Growth-of Ritonavir. Cryst. Growth Des. 2012, 12, (6), 3133-3143.
Co-pending U.S. Appl. No. 15/125,787, May 14, 2019 Final Office Action, 11 pages.
Co-pending U.S. Appl. No. 15/125,787, Response to Sep. 25, 2018 NFOA, 4 pages.
Carter, S.C.; Li, B.; Xu, D.; Edgar, K.J. "Regioselective esterification and etherification of cellulose; a review". Biomacromolecules 2011, 12, 1956-1972.
Xu, D.; Li, B.; Tate, C.; Edgar, K.J. Studies on regioselective acylation of cellulose with bulky acid chlorides. Cellulose 2011, 18, 405-419.

FIGS. 1A-C

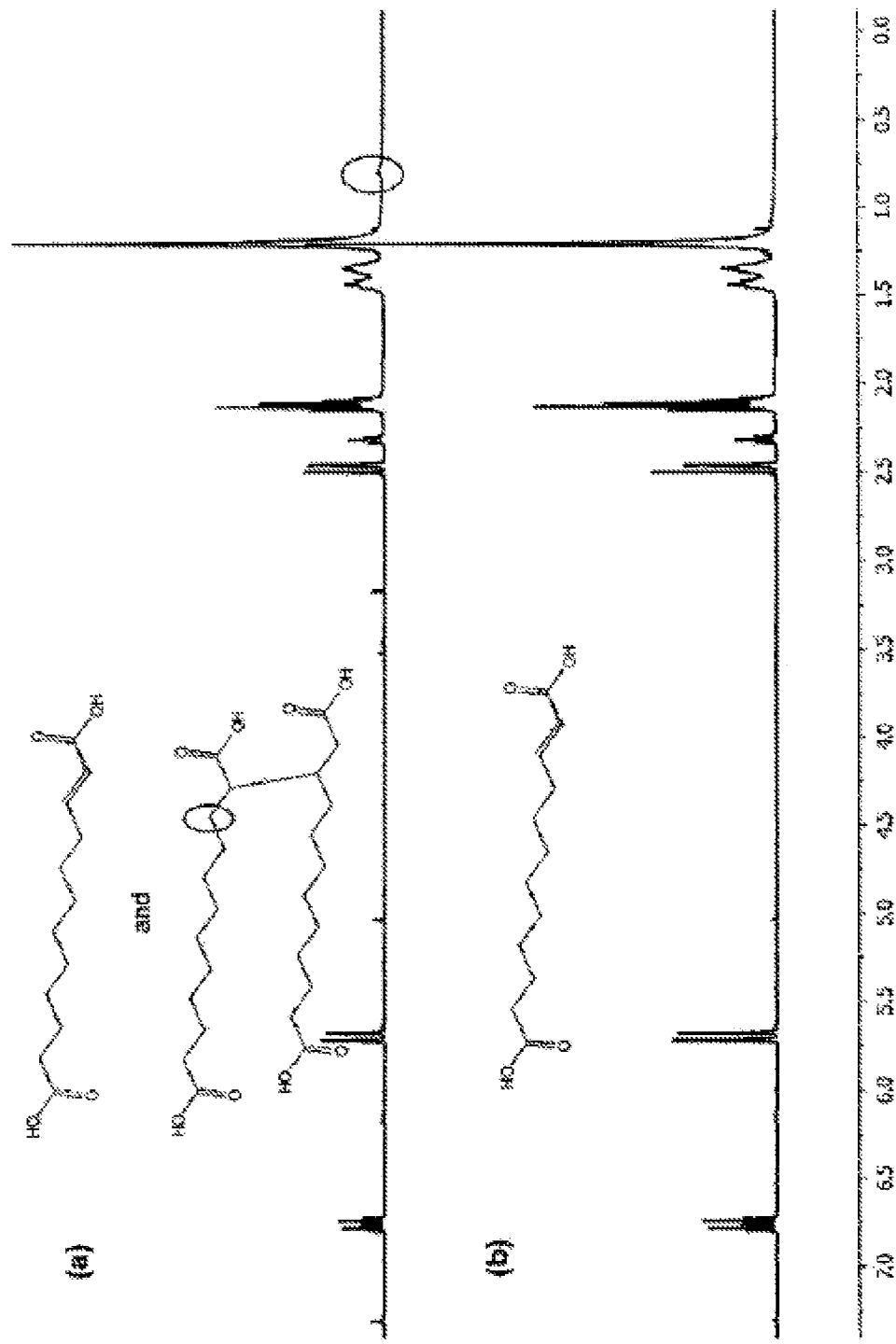
FIGS. 5A-B

CROSS-METATHESIZED POLYSACCHARIDE DERIVATIVES AND PROCESSES FOR PREPARING THEM

CROSS-REFERENCE TO RELATED APPLICATIONS

The present application is a National Stage application under 35 USC § 371 of International Application No. PCT/US14/57661, filed Sep. 26, 2014, which application relies on the disclosure of and claims priority to and the benefit of the filing date of U.S. Provisional Application No. 61/883,416, filed Sep. 27, 2013, the disclosure of which is hereby incorporated by reference herein in its entirety disclosures of each of which are hereby incorporated by reference herein in their entireties.

BACKGROUND OF THE INVENTION

Field of the Invention

The present invention relates to cross-metathesis of polysaccharides with one or more olefin-terminated side chains and cross-metathesized products thereof.

Description of Related Art

Modified polysaccharides are extremely important materials for purposes as diverse as drug delivery, adhesive tape, automobile coatings, house paint, and flat screen displays (Edgar, K. J.; Buchanan, C. M.; Debenham, J. S.; Rundquist, P. A.; Seiler, B. D.; Shelton, M. C.; Tindall. D, Advances in cellulose ester performance and application. Prog. Polym. Sci. 2001, 26, 1605-1688). Even so, modern polymer science has had little impact on increasing the variety of commercial polysaccharide derivatives available to meet current demanding materials needs. Cellulose derivatives are the most commercially important polysaccharide-based materials; nearly the entire cellulose derivative market involves derivatives with substituents selected from among just five ether types (methyl, ethyl, carboxymethyl, hydroxyethyl, and hydroxypropyl) and five ester types (acetate, propionate, butyrate, succinate, and phthalate). Furthermore, synthesis of these derivatives requires the use of somewhat forcing conditions; strong acid catalysts like sulfuric acid in the case of cellulose ester synthesis, and strong base catalysts like sodium hydroxide in the case of cellulose ether synthesis, for example. Such conditions are not conducive to reaction of the polysaccharide with sensitive moieties. The remarkable recent achievements in polymer chemistry have not been successfully applied to polysaccharides to create useful new derivatives that can be practically prepared. In order to successfully meet these demanding application needs, and to create a renewable-based economy, we must succeed in creating efficient pathways to a more diverse set of renewable polysaccharide-based materials.

Olefin metathesis has been developed in recent years as a powerful, versatile tool for the synthesis of complex small molecules, as well as the polymerization of olefinic monomers to create novel and useful polymeric structures. In olefin metathesis, metal carbene complexes are used to rearrange double bonds in carbon skeletons with high functional group tolerance and under mild reaction conditions. Although ring closing metathesis (RCM) and ring opening metathesis polymerization (ROMP) have been comprehensively investigated over the past decade, olefin cross-metathesis (CM) has become an increasingly powerful tool in both organic and polymer chemistry thanks to the publication of Grubbs' model of selectivity for CMI and the development of active and selective CM catalysts (Samojlowicz, C.; Bieniek, M.; Grela, K., Ruthenium-Based Olefin Metathesis Catalysts Bearing N-Heterocyclic Carbene Ligands. Chem. Rev. 2009, 109, (8), 3708-3742; and Vougioukalakis, G. C.; Grubbs, R. H., Synthesis and Activity of Ruthenium Olefin Metathesis Catalysts Coordinated with Thiazol-2-ylidene Ligands. J. Am. Chem. Soc. 2008, 130, (7), 2234-2245).

It is instructive that these valuable new tools have not yet been exploited for synthesis of a wide variety of new polysaccharide derivatives. Only a few related studies have appeared; one example is the work by Reddy and co-workers (Reddy, C. R.; Jithender, E.; Prasad, K. R., Total Syntheses of the Proposed Structure for Ieodoglucomides A and B. J. Org. Chem. 2013, 78, (9), 4251-4260) who successfully cross-metathesized glucose-linked olefins with amino acid-appended olefins to construct the complete carbon skeleton of ieodoglucomides A and B, two unique glycopeptides isolated from marine-derived bacteria. What about similar CM reactions between, for example, a cellulose derivative bearing unsaturated side chains, and other olefin species, which could lead to a rich variety of otherwise inaccessible derivatives? Surprisingly, only a handful of studies have described metathesis reactions of polysaccharide derivatives, and none of them have described successful CM. In a typical example, Joly et al. observed self-metathesis (SM) of cellulose 10 undecenoate using Grubbs' catalyst (1st generation), affording crosslinked and insoluble cellulose plastic films (Joly, N.; Granet, R.; Krausz, P., Olefin Metathesis Applied to Cellulose Derivatives—Synthesis, Analysis, and Properties of New Cross-linked Cellulose Plastic Films. Journal of Polymer Science Part a—Polym. Chem. 2005, 43, (2), 407-418). All such studies to date have reported dominant self-metathesis of olefin substituted polysaccharides to afford crosslinked, insoluble products. This is not surprising; metathesis of polysaccharide derivatives containing pendent olefin groups (especially reactive Type 1 olefins by Grubbs' classification) must be nearly perfectly selective for cross-metathesis rather than self-metathesis in order to avoid cross-linking that would render the polymer insoluble, difficult to melt-process, and overall very difficult to process into desired shapes. Perhaps it is the negative results of these studies that have discouraged further investigation of cross-metathesis in polysaccharide derivatives.

In order to obtain discrete, soluble, polysaccharide-olefin CM products, SM between pendant terminal olefins must be absent, and there must be a high degree of conversion to CM products. Previous studies in other systems have shown that the type of catalyst (shown in FIGS. 1A-C) used influences the ability to obtain a high degree of conversion to cross-metathesis products. The Grubbs' 1st generation catalyst (FIG. 1A) has proved to be insufficiently effective as a cross-metathesis catalyst in all but simple reactions (Rybak, A.; Meier, M. A. R., Cross-metathesis of Fatty Acid Derivatives with Methyl Acrylate: Renewable Raw Materials for the Chemical Industry. Green Chem. 2007, 9, (12), 1356-1361; and Bruneau, C.; Fischmeister, C.; Miao, X.; Malacea, R.; Dixneuf, P. H., Cross-metathesis with acrylonitrile and applications to fatty acid derivatives. Eur. J. Lipid Sci. Tech. 2010, 112, (1), 3-9).

More reactive and thermally stable Grubbs' 2nd generation (FIG. 1B) and Hoveyda-Grubbs' 2nd generation (FIG. 1C) catalysts have been heavily studied for CM reactions. Compared with Grubbs' 2nd generation, the Hoveyda-Grubbs catalyst (FIG. 1C) is more reactive towards electron-deficient olefins, and it can initiate metathesis at lower temperature. While the degree of conversion depends on the catalyst used, selectivity in CM is dependent primarily upon the structure of the reacting olefin. Based on chemical structure and reactivity results, Grubbs empirically classified olefins into 4 types (shown in Table 1) (Chatterjee, A. K.; Choi, T. L.; Sanders, D. P.; Grubbs, R. H., A General Model for Selectivity in Olefin Cross Metathesis. J. Am. Chem. Soc. 2003, 12S, (37), 11360-11370).

TABLE 1

Grubbs' Categorization of Olefins and Rules for Selectivity

| Olefin Type | Olefin Metathesis Reactivity | Examples[a] |
|---|---|---|
| Type I | Rapid homodimerization, homodimer consumable | terminal olefins |
| Type II | Slow homodimerization, homodimer sparingly consumable | acrylates, acrylic acids, acrylamides |
| Type III | No homodimerization | allylic alcohol (protected) |
| Type IV | Olefins inert to CM, but do not deactivate the catalyst (Spectator) | vinyl nitro olefins |

[a]Selectivity depends on catalyst used. The examples shown are valid for Grubbs' $2^{nd}$ generation catalyst.
Grubbs' Rules:
Reactions between two olefins of Type I = Statistical SM and CM
Reactions between two olefins of same type (non-Type 1) = Non-selective CM
Reactions between two different types (except Type IV) = Selective CM Sterically-hindered and electron-deficient olefins of type II and III have low metathesis reactivity and only slowly homodimerize, while more reactive terminal olefins (type I) readily undergo homodimerization via metathesis. Moreover, the homodimers of the terminal olefins are susceptible to subsequent secondary CM reactions. As a result, when a type I olefin is reacted with a type II or III olefin, high conversion to a CM product can be achieved by employing an excess of the type II or III olefin (Choi, T. L.; Chatterjee, A, K.; Grubbs, R. H., Synthesis of $\alpha,\beta$-Unsaturated Amides by Olefin Crossmetathesis. Angew. Chem. Int. Ed. 2001, 40, (7), 1277).

The synthesis of cellulose derivatives containing carboxyl groups has been a long-standing and fascinating challenge. One issue is the problem of synthesizing derivatives with pendant carboxyl groups attached to a polysaccharide which also contains pendant hydroxyl groups; carrying out such a transformation under the acidic conditions commonly used to manufacture cellulose esters is almost inevitably accompanied by crosslinking due to ester formation between chains. This restricts such nucleophilic substitution chemistry to near-neutral or alkaline conditions, which work well for simple cases like reaction of cellulose with succinic anhydride (Li, W. Y.; Jin, A. X.; Liu, C. F.; Sun, R. C.; Zhang, A. P.; Kennedy, J. F., Homogeneous Modification of Cellulose with Succinic Anhydride in Ionic Liquid Using 4-Dimethylaminopyridine as A Catalyst. Carbohydr. Polym. 2009, 78, (3), 389-395) or adipic anhydride (Liu, H.; Kar, N.; Edgar, K., Direct Synthesis of Cellulose Adipate Derivatives Using Adipic Anhydride. Cellulose 2012, 19, (4), 1279-1293). Attachment of ω-carboxyalkanoates in which the intervening polymethylene chain is too long for facile cyclic anhydride formation is more complicated; in the past, it has been necessary to resort to protection/deprotection methodologies (Liu, H.; Ilevbare, G. A.; Cherniawski, B. P.; Ritchie, E. T.; Taylor, L. S.; Edgar, K. J., Synthesis and Structure-Property Evaluation of Cellulose ω-Carboxyesters for Amorphous Solid Dispersions. Carbohydr. Polym., (2012), http://dx.doi.org/10.1016/j.carbpoJ.2012.11.049). Such difficulties are unfortunate since polysaccharide ω-carboxyalkanoates have many useful properties that enable important applications. In coating applications, the carboxylic acid functionality renders the derivatives water-soluble or water-dispersible, enabling waterborne and high solids coatings systems, thereby reducing the use of volatile organic solvents and enhancing coatings performance (Edgar, K. J.; Buchanan, C. M.; Debenham, J. S.; Rundquist, P. A.; Seiler. B. D.; Shelton, M. C.; Tindall, D., Advances in Cellulose Ester Performance and Application. Prog. Polym. Sci. 2001, 26, (9), 1605-1688). Cellulose derivatives containing carboxyl groups are also important components of drug delivery systems (Edgar, K. J., Cellulose Esters in Drug Delivery. Cellulose 2007, 14, (1),49-64). Since carboxylic acids have pKa values in the range of 4-5. carboxyl-containing polysaccharides are protonated in the strongly acidic environment of the stomach, and are ionized in the near-neutral small intestinal milieu. This pH-sensitivity makes the derivatives good candidates for enteric polymeric coatings or matrices, which minimize drug/stomach exposure by preventing release until the formulation reaches the higher pH environment of the small intestine. Cellulose acetate phthalate (CAPhth) was one of the first polymers used for such pH-sensitive, controlled release coatings in drug delivery (Merkle, H. P.; Speiser, P., Preparation and in Vitro Evaluation of Cellulose Acetate Phthalate Coacervate Microcapsules. J. Pharm. Sci. 1973, 62, (9), 1444-8). Other esters of cellulose with pendant carboxylic acid groups including cellulose acetate succinate (CAS) (Wilken, L. O., Jr.; Kochhar, M. M.; Bennett, D. P.; Cosgrove, F. P., Cellulose Acetate Succinate as an Enteric Coating for Some Compressed Tablets. J. Pharm. Sci. 1962, SI, 484-90), hydroxypropyl methylcellulose phthalate (HPMCP) (Kim, I. H.; Park, J. H.; Cheong, I. W.; Kim, J. H., Swelling and Drug Release Behavior of Tablets Coated with Aqueous Hydroxypropyl Methylcellulose Phthalate (HPMCP) Nanoparticles. J. Control. Release 2003, 89, (2), 225-233) and hydroxypropyl methylcellulose acetate succinate (HPMCAS) have also proven interesting for enteric coating and controlled release.

Recent studies have shown the advantages of esters of cellulose with pendant carboxylic acids in delivery of poorly soluble compounds (Biopharmaceutical Classification System (BCS) Class II), by forming miscible blends of polymers and drugs, termed amorphous solid dispersions (ASDs). These molecularly dispersed drugs generate higher solution concentrations than achievable from the corresponding crystalline drugs, by maximizing drug surface area and eliminating the need for the drug to overcome its heat of fusion in order to dissolve. Supersaturated drug solutions generated from these ASDs can not only enhance the absorption of the drug from the gastrointestinal (GI) tract, but also provide a pH-controlled release profile. For example, HPMCAS has been proven to be an effective polymer for initiating and maintaining drug supersaturation in the GI tract, stabilizing the amorphous drug against crystallization, thereby in some cases enhancing drug bioavailability (Curatolo, W.; Nightingale, J. A.; Herbig, S. M., Utility of Hydroxypropylmethyicellulose Acetate Succinate (HPMCAS) for Initiation and Maintenance of Drug Supersaturation in the GI Milieu. Pharm. Res. 2009, 26, (6), 1419-1431; and Konno, H.; Taylor, L. S., Influence of Different Polymers on the Crystallization Tendency of Molecularly Dispersed Amorphous Felodipine. J. Pharm. Sci. 2006, 95, (12), 2692-2705; B S Tanno, F.; Nishiyama, Y.; Kokubo, H.; Obara, S., Evaluation of Hypromellose Acetate Suctinate (HPMCAS) as a Carrier in Solid Dispersions. Drug Dev. Ind. Pharm. 2004, 30, (1), 9-17). More recently, the formation of ASDs of poorly water-soluble drugs and long-chain cellulose ω-carboxyalkanoates, i.e. cellulose adipate, suberate and sebacate derivatives, was investigated, and it was found that some of these polymers were highly effective at generating and maintaining supersaturated drug solutions by inhibiting nucleation and subsequent crystal growth (Ilevbare, G. A.; Liu, H.; Edgar, K. J.; Taylor, L. S., Understanding Polymer Properties Important for Crystal Growth Inhibition-Impact of Chemically Diverse Polymers on Solution Crystal Growth of Ritonavir. Cryst. Growth Des. 2012, 12, (6), 3133-3143; and Ilevbare, G. A.; Liu, H.; Edgar, K. J.; Taylor, L. S., Effect of Binary Additive Combinations on Solution Crystal Growth of the Poorly Water-Soluble Drug, Ritonavir. Cryst. Growth Des. 2012, 12, (12), 6050-6060; and Ilevbare, G. A.; Liu, H.; Edgar, K. J.; Taylor, L. S., Impact of Polymers on Crystal Growth Rate of Structurally Diverse Compounds from Aqueous Solution. Mol. Pharm. 2013, 10, (6), 2381-2393; and Ilevbare, G. A.; Liu, H.; Edgar, K. J.; Taylor, L. S., Maintaining Supersaturation in Aqueous Drug Solutions: Impact of Different Polymers on Induction Times. Cryst. Growth Des. 2013, 13, (2), 740-751). These studies also revealed that the DS of carboxylic acid functionality and the polymer hydrophobicity were key factors influencing the performance of the ASDs. The long side chains enhance the interactions of the polymers with hydrophobic drugs, while the pendant carboxylic acids provide both specific polymer-drug interactions and the pH-trigger for drug release through swelling of the ionized polymer matrix.

Thus, despite these investigations there remains a need in the art for advances in the synthesis of polysaccharide derivatives.

SUMMARY OF THE INVENTION

In embodiments, the present invention provides a method for the cross-metathesis of polysaccharides with one or more olefin-terminated side chains and cross-metathesized products thereof. In an exemplary embodiment, the present invention provides a method for the synthesis of cellulose ω-carboxyesters via olefin cross-metathesis. The prior art had been quite discouraging, in which self-metathesis dominated and insoluble, crosslinked products were obtained from similar cellulose derivatives. In contrast, the present inventors describe non-limiting examples of a method in which fully cross-metathesized products were obtained by reacting cellulose esters bearing terminal olefins, in particular cellulose alkanoate undecenoates, with acrylic acid as solvent and reagent, in THF, or in dichloromethane, employing the Hoveyda-Grubbs' 2nd generation catalyst. Crosslinking induced by intermolecular self-metathesis was avoided by using an excess of acrylic acid. While soluble products were obtained initially, loss of solubility during storage was observed and was attributed to oligomerization of the pendant α,β-unsaturated carboxylic acid groups by a free radical mechanism. The present inventors were able to suppress this free radical oligomerization and produce soluble products by addition of free radical scavengers such as BHT, thereby also creating the potential to preserve the double bond where this is desirable. Alternatively, the double bond can be hydrogenated using heterogeneous or homogeneous catalysis, resulting in a saturated, stable product; optionally this hydrogenation can be carried out in a one-pot operation without the need to isolate the metathesis product. An additional option is to react the double bond introduced in the metathesis reaction, in cases where the metathesis partner is an acrylate derivative and thus the metathesis partner has α,β-unsaturated acid, ester, or amide functionality. Addition of a nucleophile such as amine or thiol to the β-end of the double bond, called a Michael reaction, eliminates the double bond and introduces, e.g., new amine or sulfide functionality.

The method of the present invention, in an exemplary embodiment, allows for rapid, simple, versatile, highly efficient synthesis of cellulose ω-carboxyalkanoates and other polysaccharide derivatives under mild conditions. Further, embodiments of the method of the present invention include other olefin partners, and other polysaccharides containing terminal olefin groups. In addition, embodiments may include a wide variety of CM partners including but not limited to acrylic acids, acrylate esters, acrylamides, and allyl alcohols. Embodiments of the present invention provide a pathway to new families of polysaccharide derivatives with different functional groups, which can be used for structure/property studies aimed at developing polymers for drug delivery and other demanding applications. In addition, embodiments of the present invention make it possible to synthesize a series of polymer derivatives with identical Mw, DS, substitution pattern, and monosaccharide sequence, differing only in the terminal, pendant functional groups, enabling clean and enlightening investigations of structure-activity relationships.

BRIEF DESCRIPTION OF THE DRAWINGS

The accompanying drawings illustrate certain aspects of embodiments of the present invention, and should not be used to limit or define the invention. Together with the written description the drawings serve to explain certain principles of the invention.

FIGS. 5A and 5B are diagrams showing NMR spectra of alkaline hydrolysis products of cellulose esters having (FIG. 5A) and not having (FIG. 5B) solubility problems.

DETAILED DESCRIPTION OF VARIOUS EMBODIMENTS OF THE INVENTION

Figure 1:
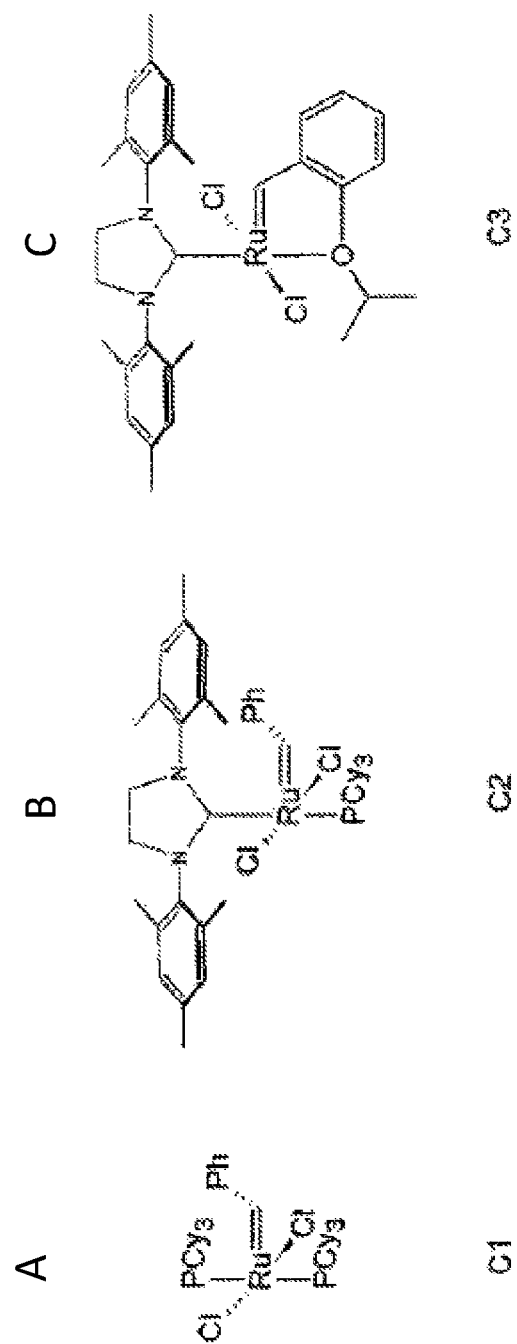
FIG. 1A is a chemical formula showing Grubbs' $1^{st}$ generation catalyst.
FIG. 1B is a chemical formula showing Grubbs' $2^{nd}$ generation catalyst.
FIG. 1C is a chemical formula showing Hoveyda-Grubbs' $2^{nd}$ generation catalyst.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

The present inventors have shown for the first time that cross-metathesis may be a useful method for the synthesis of polysaccharide derivatives. In one embodiment, the present invention provides a method for the synthesis of a cross-metathesized polysaccharide derivative, comprising: (a) providing or synthesizing a polysaccharide comprising one or more olefin-terminated side chains; (b) providing a solvent capable of dissolving the polysaccharide; (c) providing a cross-metathesis partner at a cross-metathesis partner:

terminal olefin ratio exceeding 1:1; (d) providing a catalyst, such as Hoveyda-Grubbs 2$^{nd}$ Generation Catalyst; and (e) reacting the cross-metathesis partner and the polysaccharide in the solvent for a time and under conditions sufficient to obtain a cross-metathesized product of the polysaccharide.

Embodiments of the invention include methods of synthesizing polysaccharides having one or more olefin-terminated side chains, which can be used to synthesize cross-metathesized polysaccharide derivatives. In an exemplary embodiment, the synthesized olefin-substituted polysaccharides for use as starting materials are cellulose undec-10-enoate derivatives. A detailed procedure for the synthesis of cellulose undec-10-enoate derivatives is provided in the non-limiting Example at the end of this Detailed Description. In this non-limiting Example, cellulose acetate propionate, cellulose acetate butyrate, or cellulose acetate was dissolved in 1,3 dimethyl-2-imidazolidinone or methyl ethyl ketone and heated to 60 or 90° C. under nitrogen. Triethylamine and 10-undecenoyl chloride were added and the reaction was allowed to proceed at 60 or 90° C. for 20 hours. The reaction mixture was filtered, and the filtrate was added to 50:50 water/ethyl alcohol to precipitate the product. The product was redissolved in a minimal amount of dichloromethane and reprecipitated in hexane; the product was then washed with hexane and dried under vacuum. Cellulose undec-10-enoate derivatives were prepared, including cellulose acetate undec-10-enoate, cellulose acetate propionate undec-10-enoate, and cellulose acetate butyrate undec-10-enoate.

However, this invention contemplates that other polysaccharides bearing one or more olefin-terminated side chains may be used as starting materials, either synthesized or obtained commercially. For example, the polysaccharides may be linear or branched polysaccharide or oligosaccharide molecules comprising monosaccharide, disaccharide, or trisaccharide repeating monomer units. The repeating units may be chosen from glucose, sucrose, lactose, cellobiose, mannose, ribose, galactose, arabinose, fructose, sorbose, cellobiose and raffinose. Polysaccharides of the current invention include but are not limited to cellulose, amylose, amylopectin, curdlan, pullulan, dextran, chitin, chitosan, alginic acid, xylan, glucuronoxylan, glucomannan, galactoglucomannan, pectin, chondroitin sulfate, dermatan sulfate, hyaluronic acid, heparan sulfate, and heparin. Conceivably, any polysaccharide structure bearing terminal olefins may be used as starting material. The polysaccharide may bear any type of olefin-terminated side chain such that a very wide variety of olefin groups can be used in the method. Olefin groups ranging from 2 to 50 carbon atoms having at least one carbon-carbon double bond may be used in the method, including olefin groups with 1-4 carbon atoms, 5-10 carbon atoms, 10-16 carbon atoms, 12-20 carbon atoms, 18-30 carbon atoms, or 30-50 carbon atoms, or any number of carbon atoms in between. The olefin groups may be linear or branched, and unsubstituted or substituted with one or more functional groups, such as hydroxyl, carboxyl, carbonyl, amine, amide, aldehyde, carboxylate, ester, ether, nitrate, nitroso, sulfide, and sulfydryl. The olefin groups may comprise at least one heteroatom chosen from phosphorus, sulfur, oxygen, nitrogen, boron, chlorine, bromine, iodine, and fluorine. The polysaccharides bearing olefin groups may be obtained commercially or synthesized according to procedures described in the non-limiting Example or in the scientific literature.

In embodiments, a wide variety of solvents can be used to dissolve the polysaccharide, including acetic acid, propionic acid, acrylic acid, tetrahydrofuran, dichloromethane, or trichloromethane. The particular solvent may be chosen depending on its ability to dissolve the particular polysaccharide used in the method. Additional solvents that may be used include, without limitation, $H_2O$, acetone, ethyl acetate, dimethyl sulfoxide (DMSO), dimethylformamide (DMF), N,N-dimethylacetamide (DMAc), N,N-dimethylimidazolidinone (DMI), and isopropyl alcohol. These and other solvents may be chosen based on the relative hydrophobicity or hydrophilicity of the polysaccharide or the type and number of charged groups.

In other embodiments, the method may further comprise providing a free radical scavenger. The free radical scavenger may be butylated hydroxytoluene or butylated hydroxyanisole. The free radical scavenger may be added to the solvent before or at the time that the polysaccharide is added (prior to the metathesis reaction), or it may be added to the reaction mixture at the completion of the metathesis reaction. In other embodiments, several post-CM reactions including hydrogenation, Michael addition, and thiol-ene reactions may also be performed on the CM products to get rid of the unsaturation and thus eliminate the instability of the CM product caused by the α,β-unsaturation. Hydrogenation may be performed in heterogeneous (Pd/C catalyst) or homogeneous conditions (Crabtree's or Wilkinson's catalyst) in THF to totally reduce the α,β-unsaturation without altering other functionalities ($H_2$, 30-80 psi; 3-24 hours). The α,β-unsaturation may also serve as a handle for Michael addition and thiol-ene reaction. Under catalysis of base such as triethylamine, compounds containing Michael donors such as amino and thiol groups may be added to the α,β-unsaturation. A reaction between the α,β-unsaturation and a thiol containing compound may also occur via thiol-ene mechanism where free radical initiates the reaction. In cases where mono-functional amino/thiol compounds such as 3-mercaptopropionic acid are employed, discrete adducts may be obtained along with a new functional group (carboxylic acid in the case of 3-mercaptopropionic acid). In other embodiments, the reaction between a CM product with a multi-functional amino/thiol compound such as PEG dithiol may lead to a cross-linked product, which may be useful as a hydrogel, a water-swellable film or a thermoplastic.

Once the olefin-substituted polysaccharide material has been obtained or synthesized, the cross-metathesis partner may be obtained. As used herein, the term "cross-metathesis partner" refers to a compound that undergoes a cross-metathesis reaction with a particular starting material. In embodiments of the invention, the cross-metathesis partner may be an acrylic acid, an acrylate ester (such as methyl acrylate, 2-hydroxyethyl acrylate, or poly(ethylene glycol) methyl ether acrylate), or an acrylamide (such as acrylamide, N,N-dimethylacrylamide and N-phenyl acrylamide). Thus, in some cases, such as acrylic acid, the cross-metathesis partner may serve as both solvent and cross-metathesis partner reagent. In other embodiments, the cross-metathesis partner may be an alcohol such as allyl alcohol or 3-buten-2-ol. In other embodiments, the cross-metathesis partner may be N-vinylpyrrolidone. In other embodiments, the cross-metathesis partner may be a protected allylamine such as phthalimide or succinimide-protected amines. The cross-metathesis partner could conceivably be any compound with an appropriate olefinic group. Specific cross-metathesis partners can for example include tyrenes, acrylates, acrylamides, acrylic acid, acrolein, vinyl ketones, unprotected tertiary allylic alcohols, vinyl epoxides, secondary allylic alcohols, perfluorinated alkyl olefins, 1,1-disubstituted olefins, non-bulky tri-substituted olefins, vinyl phosphonates, phenyl vinyl sulfone, quaternary allylic carbons, and protected tertiary allylic alcohols. Even further, cross-metathesis partners can be chosen from amino acids (protected or unprotected), mono-, oligo- and polysaccharides (protected or unprotected), DNA, nucleotides, or other nucleobases (protected or unprotected) that bear any of the functional groups noted above.

Embodiments of the method of the invention provide that the cross-metathesis partner is provided in excess of the terminal olefin side chain such that the cross-metathesis partner:terminal olefin ratio exceeds 1:1. In embodiments, for synthesis of certain functionalized and cross-linked products the ratio can be less than 1:1. In other embodiments, the cross-metathesis partner:terminal olefin ratio is in a range of 1:1 to 50:1 or any ratio in between, including 2:1, 4:1, 5:1, 8:1, 10:1, 12:1, 15:1, 18:1, 20:1. 25:1, 30:1, 35:1, 40:1, or 45:1. Additional information on the molar, mass, and/or volume ratio of these and other reactants may be obtained in the non-limiting Example. While not intended to be limiting, these serve as guidance for a skilled artisan to reproduce the method in their hands.

Hoveyda-Grubbs 2nd Generation Catalyst, which is known in the art, may be added, preferably once the reagents are dissolved. Its chemical structure is shown in FIG. 1C. In embodiments, the amount of Hoveyda-Grubbs 2nd Generation Catalyst may be at least 3 mol %. In other embodiments, the amount of Hoveyda-Grubbs 2nd Generation Catalyst may be in the range of 0.1 to 2 mol %, 0.5 to 5 mol %, 2 to 20 mol %, 3 to 12 mol %, 6 to 12 mol %, 4 to 8 mol %, 5 to 10 mol %, or any range in between. It is within the capabilities of a skilled artisan to choose the amount of catalyst based on the reactants used in the synthesis method. In some embodiments the catalyst is added last, in other embodiments it added prior to or with the other reagents. A skilled artisan will recognize different orders of addition of the reagents that do not sacrifice the efficiency of the reaction.

In embodiments, conditions to obtain a cross-metathesized product of the polysaccharide may be relatively mild, ranging anywhere from a temperature of room temperature to 50° C. or any temperature in between, including room temperature to 30° C., room temperature to 35° C., 30 to 35° C., 35 to 40° C., 40 to 45° C., 35 to 45° C., 30 to 50° C., 40 to 50° C., 45 to 50° C., or any range in between. Additionally, reaction times may vary from 0.5 hour to 24 hours or any time in between, including 1 to 2 hours, 1 to 3 hours, 1 to 4 hours, 1 to 5 hours, 2 to 4 hours, 3 to 6 hours, 5 to 10 hours, 10 to 20 hours, 15 to 24 hours, or any range in between. In one embodiment, the cross-metathesis reaction occurs at least at room temperature for at least one hour. The reaction may proceed by stirring the reagents under nitrogen for the stated temperatures and times. In embodiments, the reaction may be terminated by adding ethyl vinyl ether or diethylene glycol monovinyl ether. The products may be precipitated by addition of or to water or other appropriate non-solvent for the cross-metathesis product, and washed by water or other non-solvent before being dried under vacuum. In certain cases, if the CM product cannot be precipitated, dialysis may apply.

Embodiments of the invention include methods employing scaled-up reactions for use in industrial-scale cross-metathesis reactions. For example, the solvents and reagents may be provided in batch reactors with a capacity ranging from 1 liter to 15,000 liters. The solvents and reagents may be introduced by connections into the reactor and mixed by an agitator. Reaction temperatures and times may be controlled through a programmable interface. These embodiments are particularly useful for industrial scale chemical manufacture. The fast and mild nature of the cross-metathesis reaction described herein may in some cases lend itself to continuous manufacturing processes. Furthermore, with many cross-metathesis partners (e.g., acrylic acid), the excess partner reagent is unchanged under the reaction conditions, and so can be readily recovered and recycled so as to minimize waste and cost in a manufacturing process.

In an exemplary embodiment, the method of the present invention can be used for the synthesis of cellulose ω-carboxyalkanoates. A general, two-step synthetic method of cellulose ω-carboxyalkanoates is provided below (note that structures are not meant to imply regiospecificity; the particular positions of substitution are shown in all Schemes only for convenience of depiction):

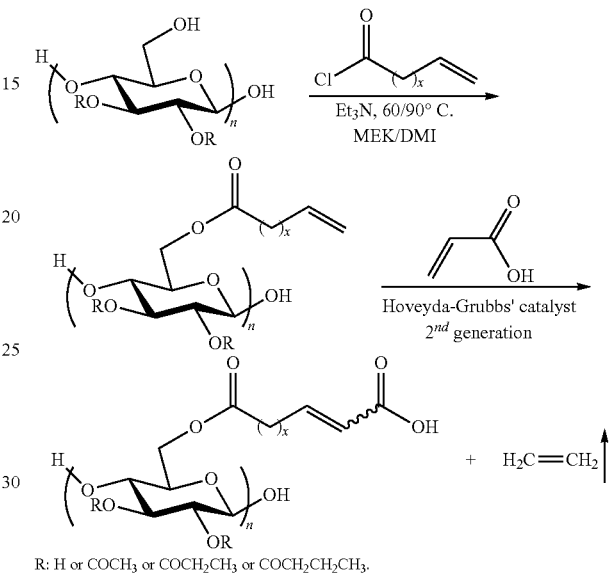

R: H or COCH$_3$ or COCH$_2$CH$_3$ or COCH$_2$CH$_2$CH$_3$.

wherein x=0-20 and n=10-10,000.

In a non-limiting Example, which will is provided in detail below, commercially available cellulose esters were first acylated with under-10-enoyl chloride, providing esters with olefin-terminated side chains. Subsequent cross-metathesis of these terminal olefin moieties with acrylic acid was performed in solvents selected from a group that includes acrylic acid, THF, DMF, DMAc, DMI, and CH$_2$Cl$_2$.

In the non-limiting Example of this disclosure, complete conversion to discrete, soluble cross-metathesis products was achieved by using an excess of acrylic acid and the Hoveyda-Grubbs' 2nd generation ruthenium catalyst. Oligomerization during storage, caused by a free radical mechanism, was observed and successfully suppressed by the addition of a free radical scavenger (BHT). Furthermore, the cross-metathesis products exhibited glass transition temperatures (T$_g$s) that were at least 50° C. higher than ambient temperature, supporting the potential for application of these polymers as amorphous solid dispersion matrices for enhancing drug aqueous solubility.

The process demonstrated in the non-limiting Example of this disclosure can be applied to any polysaccharide containing an appropriate olefinic group, in combination and reaction with any reaction partner containing an appropriate olefinic group. While no one had previously shown conditions for synthesis of discrete, soluble polysaccharide derivatives by olefin metathesis, there have been studies of olefin cross metathesis (CM) reactions of small molecules. As a result of these studies, a set of rules have been developed that are now termed "Grubbs' Rules"; these rules are the product of work in Professor Robert Grubbs' laboratory. The olefin-substituted polysaccharides and the appropriate monomeric olefin partners appear to follow Grubbs rules as summarized herein.

TABLE 2

Example combination of polysaccharides bearing terminal olefinic side-chains and CM partners.

| Example | polysaccharide | Olefinic R group | Example CM partner |
|---|---|---|---|
| Cellulose or | ![cellulose structure] | ![olefinic R, x=0-20] | ![acrylate CM partner with thymine]; or |
| Dextran or | ![dextran structure] | | ![acrylate choline]; or |
| Chitosan | ![chitosan structure] | | ![acrylamide] |

The cellulose derivatives (e.g., olefin-substituted polysaccharides) used in the non-limiting Examples of this disclosure include cellulose acetate undec-10-enoate, cellulose acetate butyrate undec-10-enoate, cellulose acetate propionate undec-10-enoate, cellulose acetate pent-4-enoate, cellulose acetate pent-4-enoate propionate, and cellulose acetate butyrate pent-4-enoate, with DS of undec-10-enoate or pent-4-enoate ranging from 0.47 to 1.28. Hoveyda-Grubbs' catalyst 2nd generation ((1,3-bis-(2,4,6-trimethylphenyl)-2-imidazolidinylidene)dichloro(o-isopropoxyphenylmethylene)ruthenium) has proven to be most useful as the olefin metathesis catalyst. In an exemplary embodiment, the conversion to CM can reach ca. 100% for CM partners including acrylic acid, acrylate esters (methyl acrylate, 2-hydroxyethyl acrylate and poly(ethylene glycol) methyl ether acrylate), and acrylamide. In other embodiments, such as for CM partners including allyl alcohol, 3-buten-2-ol, dimethyl acrylamide and N-vinylpyrrolidone, only partial CM conversions may be achieved, varying from 30 to 75%, the precise value depending mainly on catalyst loading (6~12 mol %) and solvent used. For allylamine (unprotected), no obvious cross-metathesis was observed by $^1$H NMR at 6 mol % catalyst loading; however the inventors fully expect that protected allylamines or those otherwise less able to coordinate with and deactivate the ruthenium catalyst would work well (for example phthalimide or succinimide protected amines).

In an exemplary embodiment, the present invention provides a method for the synthesis of a cellulose ω-carboxyester, having the reaction:

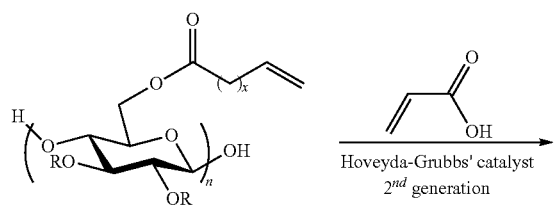

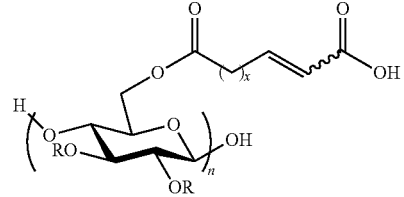

-continued wherein R is H or $COCH_3$ or $COCH_2CH_3$ or $COCH_2CH_2CH_3$; and
x=0-20 and n=10-10,000.

In an exemplary embodiment, the present invention provides a method for the synthesis of a cellulose undec-10-enoate derivative, which can be used as the olefin-substituted polysaccharide, the synthesis method having the reaction:

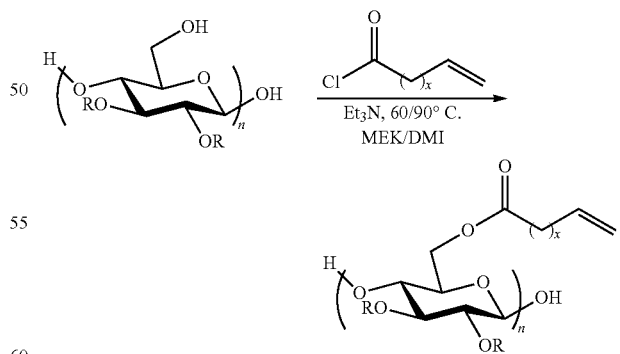

wherein: R is H or $COCH_3$ or $COCH_2CH_3$ or $COCH_2CH_2CH_3$;
$Et_3N$ is triethylamine;
MEK=methyl ethyl ketone;
DMI=1,3-dimethyl-2-imidazolidinone; and
x=0-20 and n=10-10,000.

In an exemplary embodiment, the present invention provides a cross-metathesized polysaccharide derivative having the formula:

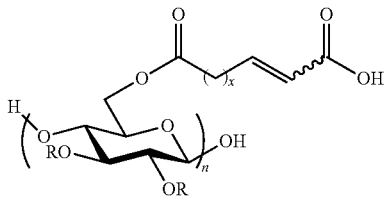

wherein R is H or $COCH_3$ or $COCH_2CH_3$ or $COCH_2CH_2CH_3$;

x=0-20 and n=10-10,000.

In an exemplary embodiment, the cross-metathesized polysaccharide derivative product is a cellulose acetate monodec-10-endioate (CADod), a cellulose acetate butyrate monododec-2-endioate (CABDod), or a cellulose acetate propionate monododec-2-endioate (CAPDod). More particularly, the cross-metathesized polysaccharide derivative product may include CADod067, CADod128, CABDod036, and CABDod051 (number refers to degree of substitution of the olefin-containing substituent modified by the metathesis reaction; 067 e.g. means 0.67 substituents per monosaccharide unit). Conceivably, the product may have a wide range of olefin densities, and is therefore not limited to these particular examples. The scope of the invention may include products of the method not described explicitly herein.

In an exemplary embodiment, the present invention provides a pharmaceutical composition comprising a cross-metathesized polysaccharide derivative described herein. The pharmaceutical composition may comprise an active pharmaceutical ingredient and a cellulose acetate monodec-10-endioate (CADod), a cellulose acetate butyrate monododec-2-endioate (CABDod), or a cellulose acetate propionate monododec-2-endioate (CAPDod), or combinations of one or more of these. The active pharmaceutical ingredient may be any agent which has pharmacological activity in a subject or patient, including a small molecule, protein, peptide, or nucleic acid.

The following Example is intended to illustrate certain principles of the invention. It is not intended to limit the scope of the invention. The principles disclosed in the Example are not limited to the particular reagents and parameters described herein and have broader applicability as recognized by a skilled artisan.

EXAMPLE

Materials. Cellulose acetate propionate (CAP-504-0.2), cellulose acetate butyrate (CAB-5530.4), and cellulose acetate (CA-320S) were from Eastman Chemical. Triethylamine ($Et_3N$) and 1,3-dimethyl-2-imidazolidinone (DMI) were purchased from Acros Organics. Toluene, N,N-dimethylformamide (DMF), N,N-dimethylacetamide (DMAc), methyl ethyl ketone (MEK) and dichloromethane were purchased from Fisher Scientific. Anhydrous tetrahydrofuran, acrylic acid, butylhydroxytoluene (BHT) and Grubbs' catalysts were purchased from Sigma Aldrich. Diethylene glycol monovinyl ether was purchased from TCI. Undec-10-enoyl chloride was purchased from Pfaltz & Bauer Inc. DMAc and DMI were dried over 4 Å molecular sieves and MEK was dried by refluxing over potassium carbonate before use. All other purchased reagents were used as received.

Measurements. $^1H$ NMR spectra were acquired on INOVA 400 or Bruker Avance 500 spectrometers operating at 400 or 500 MHz. Samples were analyzed as solutions in $CHCl_3$ or DMSO-$d_6$ (ca. 10 mg/mL) at 25° C. in standard 5 mm o.d. tubes. Three drops of trifluoroacetic acid were added to shift the water peak in DMSO-d6 downfield from the spectral region of interest. $^{13}C$ NMR and $^1H$-$^{13}C$ HSQC spectra were obtained on a Bruker Avance 500 MHz spectrometer with a minimum of 5000 scans in DMSO-d6 (ca. 50 mg/mL) at 80° C. To obtain the $T_g$ values of the cellulosic polymers, modulated DSC was performed on a TA Instruments Q2000 apparatus. Dry powders (ca. 5 mg) were loaded in Tzero™ aluminum pans. Each sample was equilibrated at −50 or −20° C. The scanning conditions were set as follows: the underlying ramp heating rate was 7° C., the oscillation amplitude was ±1° C., and oscillation period was 40 s. FUR spectra were obtained on a Nicolet 8700 instrument. Size exclusion chromatography (SEC) was performed in HPLC grade THF at 40° C. at flow rate 1 mL/min using a Waters size exclusion chromatograph equipped with an autosampler, three in-line 5 μm PLgel Mixed-C columns, and a Waters 410 refractive index (Rr) detector operating at 880 nm, which was programmed to a polystyrene calibration curve. Cellulose ester solubility was tested by adding ca. 10 mg of sample into 2 mL each of various solvents. Each mixture was subjected to vortex mixing for 510 min at room temperature, and then solubility was judged by visual examination.

Preparation of Cellulose Acetate Undec-10-enoate. CA-320S (1.00 g, 4.19 mmol/AGU) was dissolved in DMI (30 mL), and the solution was heated to 90° C. with mechanical stirring under $N_2$. Triethylamine (1.29 mL, 9.22 mmol, 2.2 equiv.; or 3.20 mL, 23.0 mmol, 5.5 equiv.) was added; a condenser was used to avoid evaporative loss of the base catalyst. Undec-10-enoyl chloride (1.70 g, 8.36 mmol, 2.0 equiv.; or 4.25 g, 20.95 mmol, 5.0 equiv.) was added dropwise and allowed to react at 90° C. for 20 h. The reaction mixture was then filtered, and the filtrate was precipitated in 300 mL 50:50 water/ethyl alcohol. The precipitate was redissolved in a minimal amount of $CH_2Cl_2$ and reprecipitated in hexane. The product was washed with hexane and dried under vacuum at 40° C.

$^1H$ NMR ($CDCl_3$):
1.22 (br s, $COCH_2CH_2C\underline{H}_2C\underline{H}_2C\underline{H}_2C\underline{H}_2CH_2CH=CH2$),
1.33 (hr s, $COCH_2CH_2CH_2CH_2CH_2CH_2C\underline{H}_2CH_2CH=CH2$),
1.53 (br s. $COCH_2C\underline{H}_2CH_2CH_2CH_2CH_2CH_2CH_2CH=CH2$).
1.88-2.03(m, $COC\underline{H}_2CH_2CH_2CH_2CH_2CH_2CH_2CH_2CH=CH2$ and $COC\underline{H}_3$),
2.26 (br s, $COC\underline{H}_2CH_2CH_2CH_2CH_2CH_2CH_2CH=CH2$),
3.25-5.24 (m, cellulose backbone),
4.85-4.94 (q, $COCH_2CH_2CH_2CH_2CH_2CH_2CH_2CH_2CH=C\underline{H}2$),
5.75 (m, o $13COCH_2CH_2CH_2CH_2CH_2CH_2CH_2C\underline{H}=CH2$).

$^{13}C$ NMR ($CDCl_3$):
20.4 ($COC\underline{H}_3$),
24.8 ($COC\underline{H}_2CH_2CH_2CH_2CH_2CH_2CH_2CH_2CH=CH2$),
28.8 ($COC\underline{H}_2C\underline{H}_2C\underline{H}_2C\underline{H}_2C\underline{H}_2C\underline{H}_2CH_2CH_2CH=CH2$),
33.6 ($COC\underline{H}_2CH_2CH_2CH_2CH_2CH_2CH_2C\underline{H}_2CH=CH2$), 114.1 (COCH$_2$CH$_2$CH$_2$CH$_2$CH$_2$CH$_2$CH$_2$CH$_2$CH=CH2),
139.0 (COCH$_2$CH$_2$CH$_2$CH$_2$CH$_2$CH$_2$CH$_2$CH$_2$CH=CH2),
168.9-173.1 (C=O),
62.2 (C-6),
72.0-76.4 (C2, C3, C5),
82.3 (C-4),
100.7 (C-I).

For the batch with 2.0 equivalents/AGU undec-10-enoyl chloride, degrees of substitution (DS) by $^1$H NMR: undec-10-enoate 0.67, acetate 1.73; yield: 93.6%. For the batch with 5.0 equivalents/AGU undec-10-enoyl chloride, DS by $^1$H NMR: undec-10-enoate 1.28, acetate 1.73; yield: 90.7%.

Preparation of Cellulose Acetate Propionate Undec-10-enoate.

CAP-504-0.2 (1.00 g, 1.78 mmol/AGU) was dissolved in MEK (20 mL), and the solution was heated to 60° C. with magnetic stirring under N$_2$. After the addition of triethylamine (0.54 mL, 1.96 mmol, 1.1 equiv.), undec-10-enoyl chloride (0.72 g, 3.56 mmol, 1.0 equiv.) was added dropwise, and the mixture was stirred for 20 h at 60° C. After filtration to remove triethylammonium chloride, the filtrate was precipitated into 300 mL 50:50 water/ethyl alcohol. Product was redissolved in CH2Cl$_2$, reprecipitated in hexane and dried under vacuum at 40° C.

Cellulose Acetate Propionate Undec-10-enoate.
$^1$H NMR (CDCl$_3$):
0.99-1.18 (m, COCH$_2$CH$_3$),
1.27-1.35 (m, COCH$_2$CH$_2$CH$^2$CH$_2$CH$_2$CH$_2$CH$_2$CH=CH$_2$),
1.55-1.63 (m, COCH$_2$CH$_2$CH$_2$CH$_2$CH$_2$CH$_1$CH$_2$CH=CH$_2$),
2.01 (m, COCH$_2$CH$_2$CH$_2$CH$_2$CH$_2$CH$_2$CH$_2$CH=CH$_2$),
2.15-2.36 (m, COCH$_3$, COCH$_2$CH$_3$, and COCH$_2$CH$_2$CH$_2$CH$_2$CH$_2$CH$_2$CH$_2$CH=CH$_2$),
3.25-5.24 (m, cellulose backbone),
4.89-4.99 (q, COCH$_2$CH$_2$CH$_2$CH$_2$CH$_2$CH$_2$CH$_2$CH=CH$_2$),
5.78 (m, COCH$_2$CH$_2$CH$_2$CH$_2$CH$_2$CH$_1$CH$_2$CH=CH$_2$).

DS by $^1$H NMR: undec-10-enoate 0.51. Yield: 94.2%.

A similar procedure was followed for the preparation of CAB undec-10-enoate.

Cellulose Acetate Butyrate Undec-10-enoate.
$^1$H NMR (CDCl$_3$):
0.87-0.97 (m, COCH$_2$CH$_2$CH$_3$),
1.27-1.35 (m, COCH$_2$CH$_2$CH$_2$CH$_2$CH$_2$CH$_2$CH$_2$CH$_2$CH=CH$_2$,
1.50-1.67 (m, COCH$_2$CH$_2$CH$_2$CH$_2$CH$_2$CH$_2$CH$_2$CH=CH$_2$, and COCH$_2$CH$_2$CH$_3$),
2.03-2.32 (m, COCH$_2$CH$_2$CH$_2$CH$_2$CH$_2$CH$_2$CH$_2$CH=CH$_2$, COCH$_2$CH$_2$CH$_3$, and COCH$_3$),
3.25-5.24 (m, cellulose backbone),
4.89-4.99 (q, COCH$_2$CH$_2$CH$_2$CH$_2$CH$_2$CH$_2$CH$_2$CH=CH$_2$),
5.78 (m, COCH$_2$CH$_2$CH$_2$CH$_2$CH$_2$CH$_2$CH$_2$CH=CH$_2$).

DS by $^1$H NMR: undec-10-enoate 0.47. Yield: 98.0%.

General Procedure for Olefin Metathesis of Cellulose Undec-10-enoate derivatives with Acrylic Acid as Solvent and Reagent. To a flask charged with cellulose undec-10-enoate derivative (100 mg, 1.0 equiv. of olefin), 5 mg BHT and 3 mL acrylic acid were added. After the reagents were completely dissolved, Hoveyda-Grubbs Catalyst 2nd Generation (0.03 equiv in THF) was added via syringe. After stirring for 1 h under N$_2$ at 30° C., the reaction was stopped by adding 1-2 drops of diethylene glycol monovinyl ether. The product was precipitated by adding to water, and the precipitate was filtered, then sufficiently washed with water before being dried under vacuum at 40° C.

General Procedure for Olefin Metathesis of Cellulose Undec-10-enoate derivatives with Acrylic Acid in THF. To a flask charged with cellulose undec-10-enoate derivatives (100 mg, 1.0 equiv. olefin), 5 mg BHT and 3 mL THF were added. After the reagents were completely dissolved, acrylic acid (20 equiv) was added followed by the addition of Hoveyda-Grubbs Catalyst 2nd Generation (0.03 equiv in THF) via syringe. After stirring for 1 h under N$_2$ at 30° C., the reaction was stopped by adding 1-2 drops of diethylene glycol monovinyl ether. The product was precipitated by addition to water, the precipitate isolated by filtration, and then sufficiently washed with water before being dried under vacuum at 40° C. Similar procedures were followed for the metathesis reaction performed in other solvent systems.

Cellulose Acetate Monododec-10-endioate
$^1$H NMR (DMSO-d$_6$):
1.23 (br s, COCH$_2$CH$_2$CH$_2$CH$_2$CH$_2$CH$_2$CH$_2$CH=CHCOOH),
1.38 (br s. COCH$_2$CH$_2$CH$_2$CH$_2$CH$_2$CH$_2$CH$_2$CH=CHCOOH),
1.50 (hr. s, COCH$_2$CH$_2$CH$_2$CH$_2$CH$_2$CH$_2$CH$_2$CH=CHCOOH),
1.86-2.14(m, COCH$_2$CH$_2$CH$_2$CH$_2$CH$_2$CH$_2$CH$_2$CH$_2$CH=CHCOOH, and COCH$_3$), 2.28 (br s. COCH$_2$CH$_2$CH$_2$CH$_2$CH$_2$CH$_2$CH$_2$CH=CHCOOH),
2.75-5.25 (m, cellulose backbone),
5.68(br s, COCH$_2$CH$_2$CH$_2$CH$_2$CH$_2$CH$_2$CH$_2$CH$_2$CH=CHCOOH, Z configuration), 5.74 (d, COCH$_2$CH$_2$CH$_2$CH$_2$CH$_2$CH$_2$CH$_2$CH$_2$CH=CHCOOH, E configuration),
6.19 (m, COCH$_2$CH$_2$CH$_2$CH$_2$CH$_2$CH$_2$CH$_2$CH$_2$CH=CHCOOH, Z configuration),
6.80 (m, COCH$_2$CH$_2$CH$_2$CH$_2$CH$_2$CH$_2$CH$_2$CH$_2$CH=CHCOOH, E configuration).

$^{13}$C NMR (DMSO-d6):
20.7 (COCH3),
24.8 (COCH$_2$CH$_2$CH$_2$CH$_2$CH$_2$CH$_2$CH$_2$CH=CHCOOH),
28.0 (COCH$_2$CH$_2$CH$_2$CH$_2$CH$_2$CH$_2$CH$_2$CH=CHCOOH),
29.0 (COCH$_2$CH$_2$CH$_2$CH$_2$CH$_2$CH$_2$CH$_2$CH=CHCOOH),
31.8 (COCH$_2$CH$_2$CH$_2$CH$_2$CH$_2$CH$_2$CH$_2$CH$_2$CH=CHCOOH),
33.8 (COCH$_2$CH$_2$CH$_2$CH$_2$CH$_2$CH$_2$CH$_2$CH=CHCOOH),
122.4 (COCH$_2$CH$_2$CH$_2$CH$_2$CH$_2$CH$_2$CH$_2$CH=CHCOOH),
149.0 (COCH$_2$CH$_2$CH$_2$CH$_2$CH$_2$CH$_2$CH$_2$CH=CHCOOH),
167.4 (COCH$_2$CH$_2$CH$_2$CH$_2$CH$_2$CH$_2$CH$_2$CH=CHCOOH),
169.1-173.3 (C=O),
63.0 (C-6),
72.0-76.4 (C2, C3, C5),
80.4 (C-4),
100.0 (C-1).

For cellulose acetate undec-10-enoate with DS of 0.67, conversion by $^1$H NMR: 100%, E/Z ratio by $^1$H NMR: 16.7, yield: 92.6%. For celluloseacetate undec-10-enoate with DS of 1.28, conversion by $^1$H NMR: 100%, E/Z ratio by $^1$H NMR: 4.0, yield: 71.0%.

Cellulose Acetate Butyrate Monododec-2-endioate
$^1$H NMR (DMSO-d$_6$):
0.83-0.91 (m, COCH$_2$CH$_2$C$\underline{H}_3$),
1.26 (br s, COCH$_2$CH$_2$C$\underline{H}_2$CH$_2$CH$_2$C$\underline{H}_2$CH$_2$CH$_2$CH=CHCOOH).
1.38 (br s, COCH$_2$CH$_2$CH$_2$CH$_2$CH$_2$CH$_2$C$\underline{H}_2$CH$_2$CH=CHCOOH),
1.50 (br. s, COCH$_2$CH$_2$CH$_2$CH$_2$CH$_2$CH$_2$CH$_2$CH$_2$CH=CHCOOH),
1.86-2.14 (m, COCH$_2$C$\underline{H}_2$CH$_2$CH$_2$CH$_2$CH$_2$CH$_2$CH=CHCOOH, and COC$\underline{H}_3$),
2.28 (br s, COCH$_2$CH$_2$CH$_2$CH$_2$CH$_2$CH$_2$C$\underline{H}_2$CH=CHCOOH), 2.75-5.25 (m, cellulose backbone),
5.68 (br s. COCH$_2$CH$_2$CH$_2$CH$_2$CH$_2$CH$_2$CH$_2$CH=C$\underline{H}$COOH, Z configuration),
5.73 (d, COCH$_2$CH$_2$CH$_2$CH$_2$CH$_2$CH$_2$CH$_2$CH=C$\underline{H}$COOH, E configuration),
6.19 (m, COCH$_2$CH$_2$CH$_2$CH$_2$CH$_2$CH$_2$CH$_2$C$\underline{H}$=CHCOOH, Z configuration),
6.79 (m, COCH$_2$CH$_2$CH$_2$CH$_2$CH$_2$CH$_2$CH$_2$C$\underline{H}$=CHCOOH, E configuration).

Conversion by $^1$H NMR: 100%, E/Z ratio by $^1$H NMR: –5, yield: 85.2%.

Cellulose Acetate Propionate monododec-2-endioate
$^1$H NMR (DMSO-d$_6$):
0.93-1.04 (m, COCH$_2$C$\underline{H}_3$),
1.24 (br s, COCH$_2$CH$_2$C$\underline{H}_2$CH$_2$CH$_2$C$\underline{H}_2$CH$_2$CH$_2$CH=CHCOOH),
1.37 (br s, COCH$_2$CH$_2$CH$_2$CH$_2$CH$_2$CH$_2$C$\underline{H}_2$CH=CHCOOH),
1.48 (hr. s, COCH$_2$C$\underline{H}_2$CH$_2$CH$_2$CH$_2$CH$_2$CH$_2$CH=CHCOOH),
2.13-2.29 (m, COC$\underline{H}_2$CH$_2$CH$_2$CH$_2$CH$_2$CH$_2$C$\underline{H}_2$CH=CHCOOH and COC$\underline{H}_3$).
2.75-5.25 (m, cellulose backbone),
5.68 (br s, COCH$_2$CH$_2$CH$_2$CH$_2$CH$_2$CH$_2$CH$_2$CH=C$\underline{H}$COOH. Z configuration),
5.72 (d, COCH$_2$CH$_2$CH$_2$CH$_2$CH$_2$CH$_2$CH$_2$CH=C$\underline{H}$COOH, E configuration),
6.18 (m, COCH$_2$CH$_2$CH$_2$CH$_2$CH$_2$CH$_2$CH$_2$C$\underline{H}$=CHCOOH, Z configuration),
6.79 (m, COCH$_2$CH$_2$CH$_2$CH$_2$CH$_2$CH$_2$CH$_2$C$\underline{H}$=CHCOOH, E configuration).

Conversion by $^1$H NMR: 100%, E/Z ratio by $^1$H NMR: 20.0, yield: 95.2%.

Results and Discussion

Terminally-unsaturated fatty acids are type I olefins in Grubbs' classification, prone to rapid homodimerization. Many researchers have studied CM of such small molecules with methyl acrylate (Djigoue, G. B.; Meier, M. A. R., Improving the Selectivity for the Synthesis of Two Renewable Platform Chemicals via Olefin Metathesis. Appl. Catal. A-Gen. 2009, 368, (1-2), 158-162; and Miao, X.; Fischmeister, C.; Dixneuf, P. H.; Bruneau, c.; Dubois, J. L.; Couturier, J. L., Polyamide Precursors from Renewable 10-Undecenenitrile and Methyl Acrylate via Olefin Cross-metathesis. Green Chem. 2012, 14, (8), 2179-2183 ("Miao et al.")). acrylonitrile ("Miao et al."), allyl chloride ("Miao et al.") and alkynes (Le Ravalec, V.; Dupe, A.; Fischmeister, C.; Bruneau, C., Improving Sustainability in Ene-Yne Cross-Metathesis for Transformation of Unsaturated Fatty Esters. Chemsuschem 2010, 3, (11), 1291-1297), leading to a variety of end functionalized fatty acids. In fact, terminally-unsaturated fatty acids can be made by cross metathesis between unsaturated fatty acids from natural oils and ethylene (Rybak, A.; Fokou, P. A.; Meier, M. A. R., Metathesis as a Versatile Tool in Oleochemistry. Eur. J. Lipid Sci. Technol. 2008, 110, (9), 797-804). The present inventors prepared esters of cellulose containing long chain esters with terminal unsaturation (CA-, CAB-, CAP-10-undecenoate) by methods similar to those previously used for synthesis of esters of cellulose with saturated long chain acids (Liu, H.; Hevbare, G. A.; Cherniawski, B. P.; Ritchie. E. T.; Taylor, L. S.; Edgar, K. J., Synthesis and Structure-Property Evaluation of Cellulose ω-Carboxyesters for Amorphous Solid Dispersions. Carbohydr. Polym., (2012); and Edgar, K. J.; Buchanan, C. M.; Debenham, J. S.; Rundquist, P. A.; Seiler, B. D.; Shelton, M. C.; Tindall, D., Advances in Cellulose Ester Performance and Application. Prog. Polym. Sci. 2001, 26, (9), 1605-1688; and Edgar, K. J., Cellulose Esters in Drug Delivery. Cellulose 2007, 14, (1),49-64; and Wilken, L. O., Jr.; Kochhar, M. M.; Bennett, D. P.; Cosgrove, F. P., Cellulose Acetate Succinate as an Enteric Coating for Some Compressed Tablets. J. Pharm. Sci. 1962, S1, 484-90; and Crepy, L.; Chaveriat, L.; Banoub, J.; Martin, P.; Joly, N., Synthesis of Cellulose Fatty Esters as Plastics-Influence of the Degree of Substitution and the Fatty Chain Length on Mechanical Properties. Chemsuschem 2009, 2, (2), 165-170) in particular by esterifying commercially available cellulose esters with undec-10-enoyl chloride in the presence of Et$_3$N (Table 3).

TABLE 3

Synthesis of Cellulose Ester Undec-10-enoates

| Sample | Starting cellulose ester | Solvent | Molar ratio[a] | Temp. (° C.) | DS (Un)[b] | DS (other)[c] | Product |
|---|---|---|---|---|---|---|---|
| 1 | CA-320S | DMI | 2.0 | 90 | 0.67 | Ac 1.82, 1.72[b] | CA-U067 |
| 2 | CA320S | DMI | 5.0 | 90 | 1.28 | Ac 1.82, 1.72[b] | CA-U128 |
| 3 | CAB-553-0.4 | MEK | 1.0 | 60 | 0.47 | Ac 0.14, Bu 1.99 | CAB-U047 |
| 4 | CAP-504-0.2 | MEK | 1.0 | 60 | 0.51 | Ac 0.04, Pr 2.09 | CAP-U051 |

[a]Mol 10-undecenoyl chloride per mol anhydroglucose unit.
[b]Determined by $^1$H-NMR.
[c]Reported in a previous publication[14]

DS(undec-10-enoate) (DS(Un)) of adducts with CA, CAB, and CAP was kept mostly in the range 0.4 to 0.7 in order to obtain derivatives with relatively high glass-transition temperature ($T_g$) values, advantageous for minimizing drug mobility and thus crystallization in ASD formulations (Glasser, W. G.; Samaranayake, G.; Dumay, M.; Dave, V., Novel Cellulose Derivatives. III. Thermal Analysis of Mixed Esters with Butyric and Hexanoic Acid. J. Polym. Sci. Phys. 1995, 33, (14), 2045-2054; and Weuts, I.; Van Dycke, F.; Voorspoels, J.; De Cort, S.; Stokbroekx, S.; Leemans, R.; Brewster, M. E.; Xu, D.; Segmuller, B.; Turner, Y. T. A.; Roberts, C. J.; Davies, M. C.; Qi, S.; Craig, D. Q. M.; Reading, M., Physicochemical Properties of the Amorphous Drug, Cast Films, and Spray Dried Powders to Predict Formulation Probability of Success for Solid Dispersions: Etravirine. J. Pharm. Sci. 2011, 100, (1), 260-274). One higher DS(Un) sample (DS 1.28) was prepared in order to examine whether the CM reaction would still be effective at higher olefin densities.

For successful synthesis of soluble, uncrosslinked cellulose ω-carboxyalkanoates, the present inventors needed to maximize CM between the terminal olefin of the cellulose alkanoate undecenoate and acrylic acid, and suppress SM of both starting materials and products. The present inventors explored the impact of several factors known to be important in CM of small molecules, including catalyst type and loading, stoichiometry, and reaction time and temperature (Table 4).

Figure 3A:
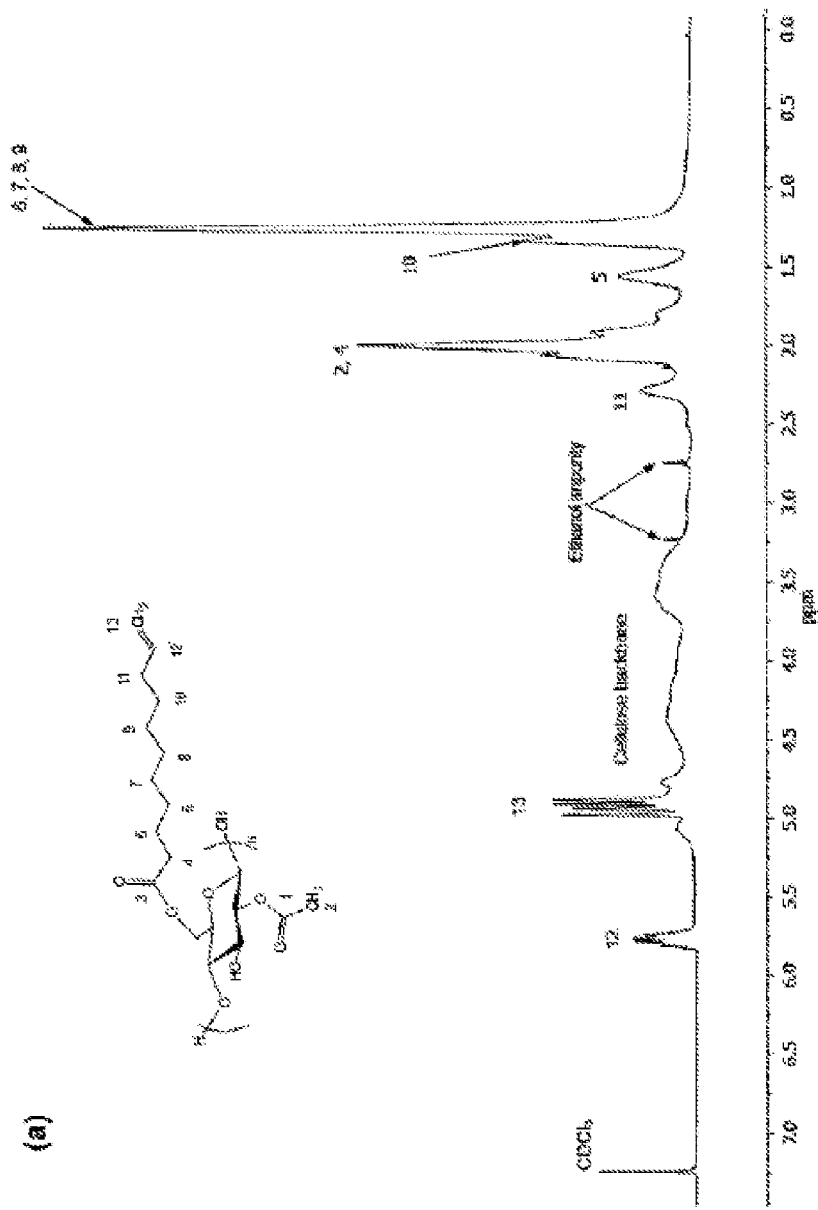
FIGS. 3A and 3B are diagrams showing $^1$H NMR spectra of CA-U067 (FIG. 3A) and CAU067MAA (FIG. 3B).
Figure 3B:
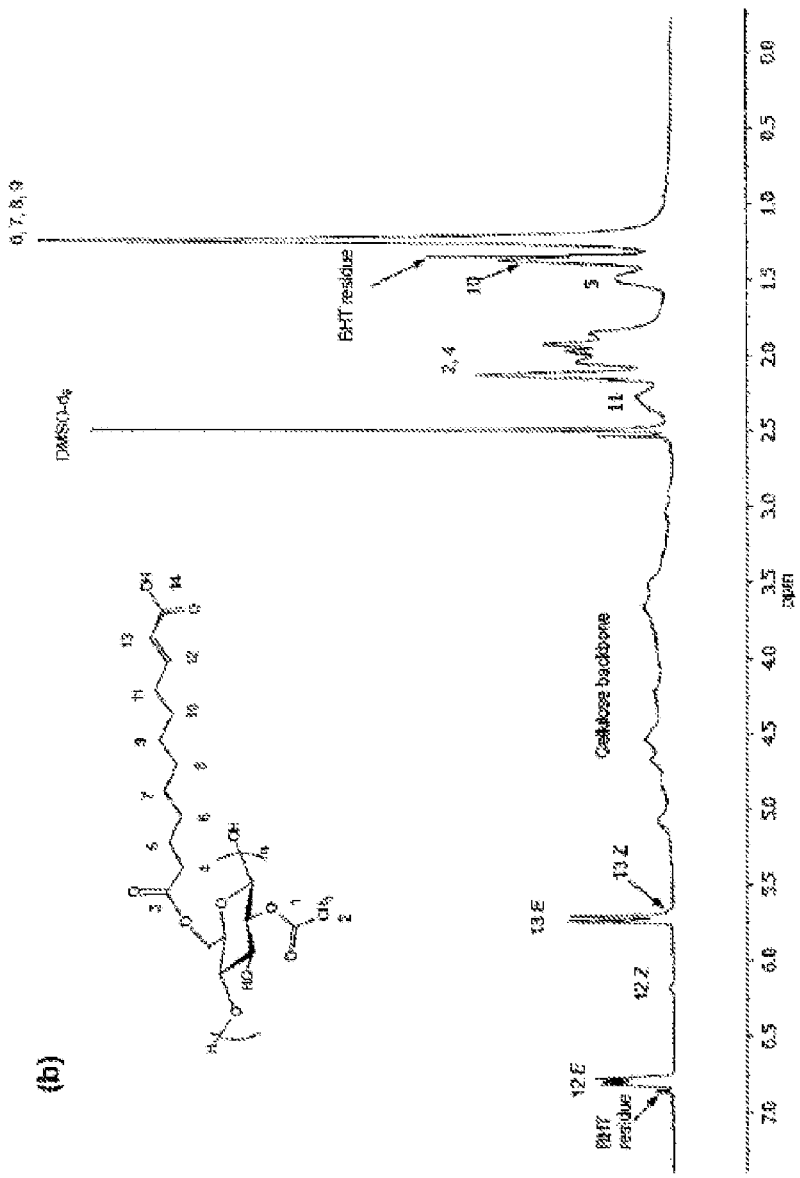
Figure 4A:
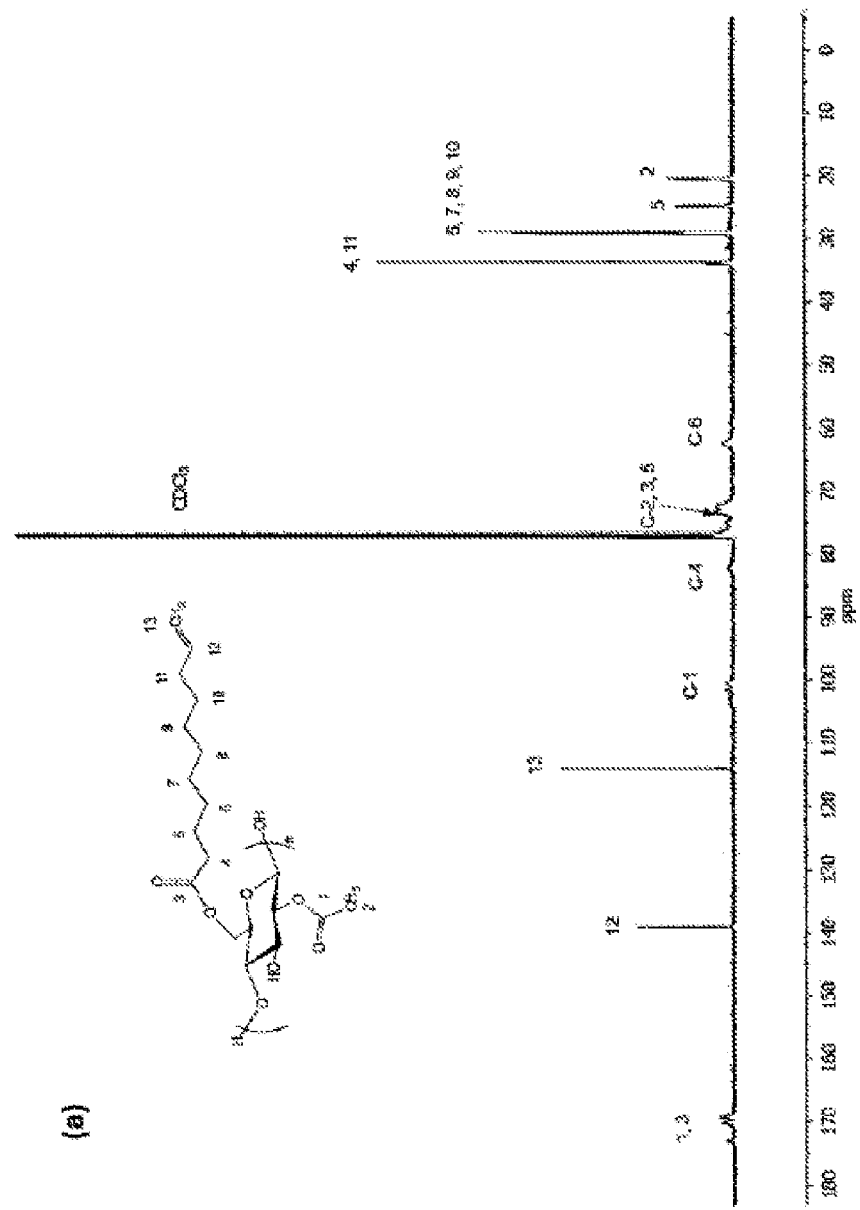
FIGS. 4A and 4B are diagrams showing $^{13}$C NMR spectra of CA-U067 (FIG. 4A) and CAU067MAA (FIG. 4B).
Figure 4B:
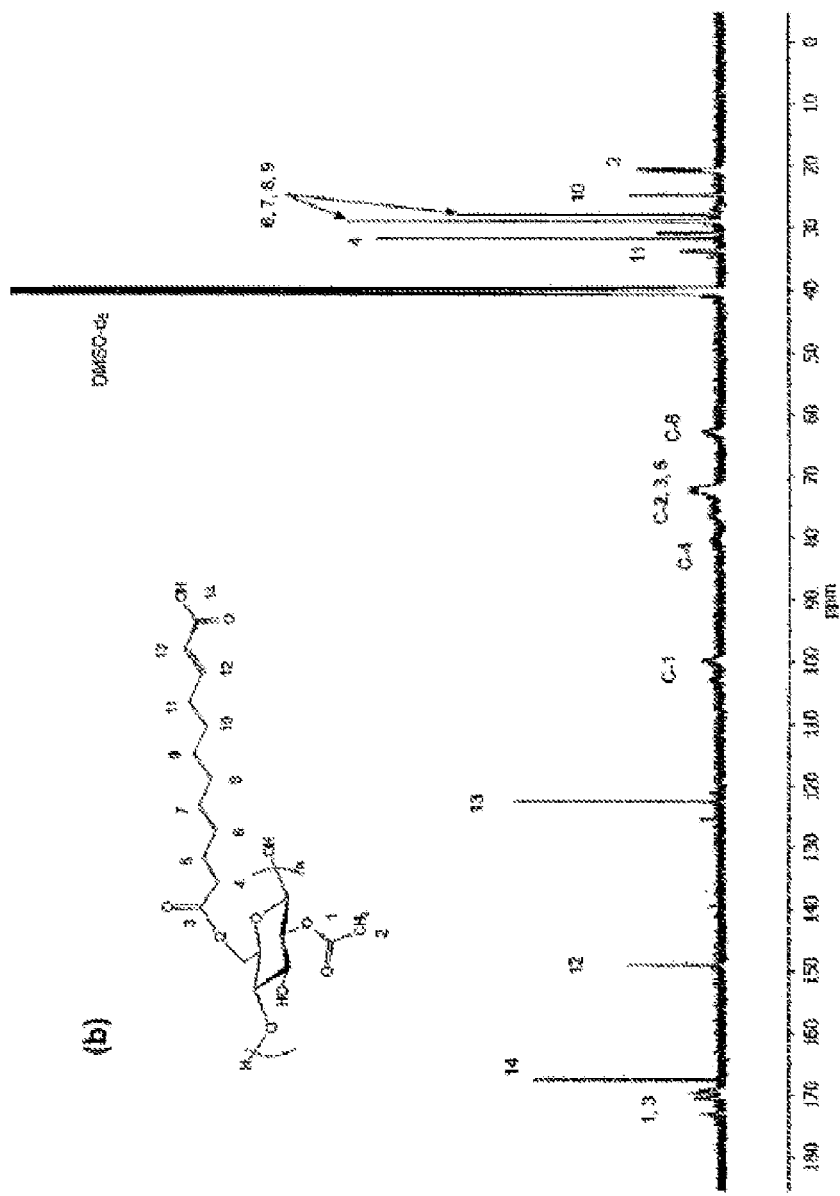

1650 $cm^{-1}$ after CM. The appearance of a C=O stretch absorbance at 1694 $cm^{-1}$ on the shoulder of the ester c=o stretch peak at 1751 $cm^{-1}$ was also observed, further supporting the success of CM. Proton NMR was a useful tool for following the reaction (FIGS. 3A and 3B), by following disappearance of the terminal olefin protons of the starting material at 4.90 and 5.75 ppm. New proton signals appeared at 5.73 and 6.80 ppm, which were assigned to protons of the α,β-unsaturated carboxylic acid in its E configuration. Correspondingly, the signals of the product olefin in the Z configuration were found at 5.68 and 6.19. $^{13}$C NMR spectra (FIGS. 4A and 4B) showed the complete disappearance of starting terminal olefin signals at 114 and 139 ppm, and the appearance of new peaks at 122 and 149 ppm, supporting the conclusion that 100% CM conversion had occurred. To further confirm the assignment of proton peaks of E/Z configuration, $^1$G-$^{13}$C HSQC was performed, which showed correlation of the carbon signal at 122 ppm with proton signals at 5.73 and 5.68 ppm, and correlation of the carbon signal at 149 ppm with proton signals at 6.80 and 6.19 ppm. Integration of the $^1$H NMR spectrum showed that the E configuration was obtained in strong preference to the Z configuration, which is inconsistent with previous reports (Choi, T. L.; Chatterjee, A, K.; Grubbs, R. H., Synthesis of α,β-Unsaturated Amides by Olefin Crossmetathesis. Angew. Chem. Int. Ed. 2001, 40, (7), 1277; and Djigoue, G. B.; Meier, M. A. R., Improving the Selectivity for the Synthesis of Two Renewable Platform Chemicals via Olefin Metath-

TABLE 4

CM of Cellulose Undec-10-enoate Derivatives With Acrylic Acid

| Exp. | Start. mat. | Cat. type | Cat. Load. (mol %) | Solvent | Mol. ratio [a] | Temp. (° C.) | Time (h) | Conv. | Product |
|---|---|---|---|---|---|---|---|---|---|
| 1 | CA-U067 | C2 | 2 | AA | — | 50 | 24 | ~0 | — |
| 2 | CA-U067 | C3 | 2 | AA | — | 50 | 24 | ~90 | — |
| 3 | CA-U067 | C3 | 3 | AA | — | 30/r.t. | 0.5/1 | ~100 | CAU067MAA |
| 4 | CA-U128 | C3 | 3 | AA | — | 30 | 1 | ~100 | CAU128MAA |
| 5 | CA-U067 | C3 | 3 | DCM | 1:5 | 30 | 1 | N.A.[b] | — |
| 6 | CA-U067 | C3 | 3 | DCM | 1:20 | 30 | 1 | ~100 | CAU067MAA CH$_2$Cl$_2$ |
| 7 | CA-U067 | C3 | 3 | CHCl$_3$ | 1:20 | 30 | 1 | ~90[b] | — |
| 8 | CA-U067 | C3 | 3 | THF | 1:5 | 30 | 1 | ~90 | — |
| 9 | CA-U067 | C3 | 3 | THF | 1:20 | 30 | 1 | ~100 | CAU067MAATHF |
| 10 | CAB-U047 | C3 | 3 | AA | — | r.t. | 1 | ~100 | CABU047MAA |
| 11 | CAP-U051 | C3 | 3 | AA | — | r.t. | 1 | ~100 | CAPU051MAA |

[a] mol of terminal double bond:mol of acrylic acid.
[b] Gelation was observed during the reaction.

Figure 2:
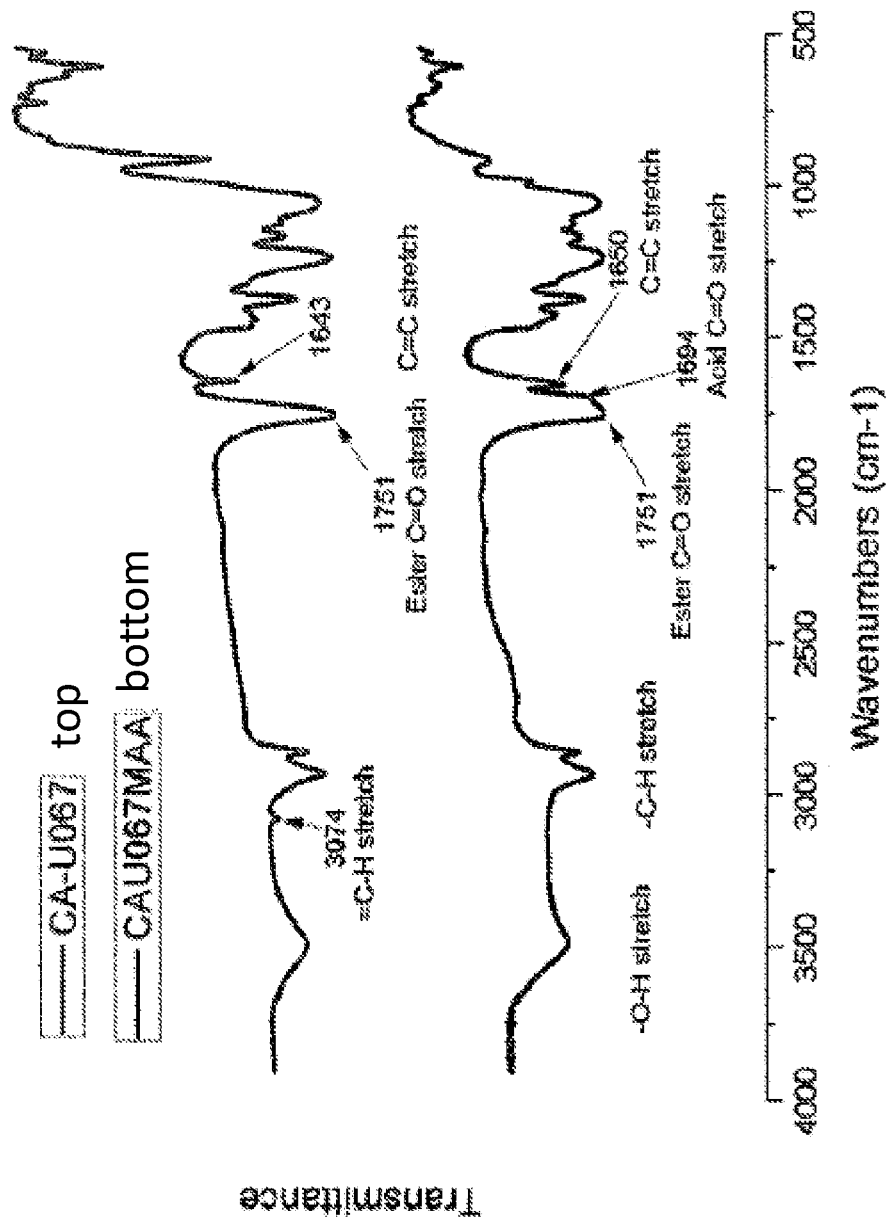
FIG. 2 is a diagram showing FTIR spectra of CA-U067 and CAU067MAA.

Grubbs' 2nd generation catalyst (C2) and Hoveyda-Grubbs' 2nd generation catalyst (C3) were compared using CA-U067 as starting material and acrylic acid as both reagent and solvent. Clearly C3 was much more effective than C2 (Exp. 1, 2) in this system. Catalyst loading also significantly affected CM conversion (characterized herein as the percent of the terminal olefin groups that underwent CM); 2 mol % C3 afforded ~90% conversion, while the present inventors were gratified to observe that 3 mol % catalyst loading gave complete conversion, even under very mild conditions (room temperature) and with rapid kinetics (complete in 30 min). Such mild conditions and short reaction times were encouraging for cases in which acrylic acid was used as both reactant and solvent, promising to minimize any acid-catalyzed solvolysis of glycosidic linkages. From the FTIR spectra (FIG. 2), it can be seen that the peak at 1643 $cm^{-1}$ which was assigned to the C=C stretch of the starting cellulose ester undecenoates, was shifted to esis. Appl. Catal. A-Gen. 2009, 368, (1-2), 158-162; and Miao, X.; Fischmeister, C.; Dixneuf, P. H.; Bruneau, C.; Dubois, J. L.; Couturier, J. L., Polyamide Precursors from Renewable 10-Undecenenitrile and Methyl Acrylate via Olefin Cross-metathesis. Green Chem. 2012, 14, (8), 2179-2183). However, the E/Z ratio for the CA product was observed to vary from experiment to experiment; this phenomenon was also observed in reactions of CAB and CAP undecenoates. It should be noted that to whatever extent the E/Z mixture is an issue for a particular application, it could be alleviated by subsequently subjecting the product α,β-unsaturated carboxylic acids to reactions such as Michael addition (Miyata, O.; Shinada, T.; Ninomiya, I.; Naito, T.; Date, T.; Okamura, K.; Inagaki, S., Stereospecific nucleophilic addition reactions to olefins. Addition of Thiols to α,β-Unsaturated Carboxylic Acid Derivatives. J. Org. Chem. 1991, 56, (23), 6556-6564) or hydrogenation (Mori, A.; Miyakawa, Y.; Ohashi, E.; Haga, T.; Maegawa, T.; Sajiki, H., Pd/C-catalyzed chemoselective hydrogenation in the presence of diphenylsulfide. Org. Lett. 2006, 8, (15), 3279-3281) that would eliminate the double bond. Highly selective cross-metathesis with CAB-U047, CAP-U05I and CA-UI28 was also observed under similar conditions, also reaching 100% conversion ($^1$H NMR). Even in the case of CM of acrylic acid with CA-UI28, which has nearly twice the olefin density of CA-U067, 100% CM was observed, with no sign of crosslinking.

The present inventors were pleased with the success of the CM reaction in acrylic acid as reagent and solvent, but were watchful about two potential problems: 1) the possibility of acid-catalyzed solvolysis of the glycosidic linkages due to the preponderance of acrylic acid, and 2) the possibility that other terminal and electron-deficient olefins might be incompatible with acrylic acid solvent due to solubility or miscibility issues (e.g. acrylamide, unpublished results). For these reasons, other solvent systems were investigated using CA-U067 as starting material. Dichloromethane, commonly used as an OM solvent, was investigated first. However, with an acrylic acid: terminal olefin ratio of 5:1 and all other conditions the same as those in acrylic acid solvent, gelation was observed at the end of the reaction, indicating the possibility that substantial intermolecular SM had occurred. Upon using THF as solvent and an acrylic acid: terminal olefin ratio of 5:1, incomplete CM (~90% conversion) was observed, though there was no gelation. Increasing the acrylic acid: olefin ratio to 20:1 afforded completely cross-metathesized products in either $CH_2Cl_2$ or THF. In contrast, incomplete CM and slight gelation were observed under the same conditions when $CHCl_3$ was used as solvent. The results obtained in different solvents can be rationalized by a change in polymer solubility as a result of the CM reaction. Although the starting polymer was readily soluble in either $CH_2Cl_2$ or $CHCl_3$ (Table 5), the acrylic acid CM product was no longer soluble in these solvents.

TABLE 5

Solubility of Cellulose Undec-10-enoate Derivatives and Cellulose Monododec-10-endioate Derivatives in Various Solvents

| Solvent | $CH_2Cl_2$ | $CHCl_3$ | EtOAc | iPrOH | THF | Acetone | DMSO | DMF |
|---|---|---|---|---|---|---|---|---|
| CA-U067 | + | + | + | − | + | + | + | + |
| CAU067MAA | − | − | − | − | + | + | + | + |
| CA-U128 | + | + | + | − | + | + | + | + |
| CAU128MAA | P | P | + | − | + | + | + | + |
| CAB-U047 | + | + | + | − | + | + | + | + |
| CABU047MAA | P | P | + | − | + | + | + | + |
| CAP-U051 | + | + | + | − | + | + | + | + |
| CAPU051MAA | P | P | + | − | + | + | + | + |

+ soluble;
− insoluble;
P partially soluble

While the polymer may not necessarily precipitate as the reaction proceeds, its decreased solubility may cause it to aggregate, increasing the likelihood of intra- and intermolecular SM. THF, on the other hand, is a good solvent for both the starting material and the final product. As a result, no precipitation, aggregation, or aggregation-induced SM is observed in THF.

SEC was used to determine the degree of molecular weight change during the reaction (Table 6).

TABLE 6

Molecular Weight and $T_g$ of the Cellulose Esters

| Sample | Mn (kDa) | Mw (kDa) | PDI | $T_g$ (° C.) |
|---|---|---|---|---|
| CA-320S | 38.0[a] | NA | NA | 180[b] |
| CA-U067 | 36.8 | 72.8 | 1.98 | — |
| CAU067MAA | 16.4 | 25.5 | 1.56 | 115 |
| CAU067MAATHF | 26.6 | 57.7 | 2.16 | 109 |
| CA-U128 | 25.4 | 43.6 | 1.72 | — |
| CAU128MAA | 19.9 | 27.0 | 1.36 | −15, 94 |
| CAB-553-04 | 20.0[a]/22.1 | 56.3 | 2.54 | 100[b] |
| CAB-U047 | 24.8 | 55.5 | 2.24 | — |
| CABU047MAA | 23.4 | 52.7 | 2.25 | 93 |
| CAP-504-02 | 15.0[a]/15.2 | 31.0 | 2.04 | 158[b] |
| CAP-U051 | 17.7 | 34.0 | 1.92 | — |
| CAPU051MAA | 16.4 | 30.6 | 1.86 | 81 |

[a]Data reported by supplier, versus polystyrene standards.
[b]Data reported in previous publication[28].

Polydispersity index (PDI) data from SEC chromatograms can be used as an indicator of intermolecular SM. While a decreased PDI indicates some degree of chain scission, an increased PDI can be interpreted as a sign of chain coupling and crosslinking. For CAB-U047, CAP-U051 and CA-UI28, polymer molecular weights decreased slightly after 1 h reaction in acrylic acid at either room temperature or 30° C., showing that the mild reaction conditions did preserve polymer molecular weight even in an acidic solvent. The observed slight decrease in PDI strongly indicated that intermolecular SM was successfully suppressed. As for CA-U067, its higher starting chain length and shorter side chain esters (acetate) compared with the butyrate and propionate derivatives render it more susceptible to chain scission catalyzed by acids. As a result, more than 50% loss of Mn was observed after reaction of CA-U067 for 1 h at 30° C. in acrylic acid solvent. Performing the reaction in THF preserved DP to some extent (30% loss of Mn). However, PDI increased from 1.98 to 2.16, possibly due to a small amount of chain coupling caused by intermolecular SM.

Polymer glass transition temperature is an important parameter influencing the potential for its use as an ASD matrix. As the glassy state restricts drug mobility and resulting crystallization, a polymer with $T_g$ that is at least 50° C. higher than ambient temperature is preferred in ASD formulations. This keeps the formulation $T_g$ above ambient temperature in spite of the plasticizing effects of both drug and atmospheric moisture. For the long chain CM product synthesized herein, only very weak thermal transitions were observed by standard DSC methods. Modulated DSC was employed to give sharper transitions (Table 6). Although the $T_g$ values of the CM products decreased 10 to 80° C. compared with those of the starting cellulose esters, they still remained at least 50° C. higher than room temperature. As expected, the higher DS of long side chain produced a lower $T_g$ value for CAU128MAA than that for CAU067MAA. The high DS CM product CAU128MAA also displayed an extra low temperature transition at 15° C., which the inventors attribute to cooperative motion of the long side chains by analogy to results from other studies of long chain cellulose esters (Kar, N.; Liu, H.; Edgar, K. J., Synthesis of Cellulose Adipate Derivatives. Biomacromolecules 2011; and Sealey, J. E.; Samaranayake, G.; Todd, J. G.; Glasser, W. G., Novel Cellulose Derivatives. IV. Preparation and Thermal Analysis of Waxy Esters of Cellulose. J. Polym. Sc. Phys. 1996, 34, (9), 1613-1620).

During the investigation of the CM reaction, an intriguing and disturbing phenomenon was observed. CM products lost solubility during storage, and the polymer with higher DS of $\alpha,\beta$ unsaturated carboxylic acid lost solubility faster than those with lower DS. Moreover, dissolving the originally soluble polymer in THF and then precipitating it in hexane in some cases generated insoluble product immediately. Apparently, certain reaction(s) caused rapid, substantial crosslinking, and the crosslinking had something to do with the $\alpha,\beta$ unsaturated carboxylic acid groups. The present inventors were concerned about the possibility of continuing, secondary metathesis of the pendant $\alpha,\beta$ unsaturated carboxylic acid groups of the product, which could be caused by residual catalyst. To exclude this possibility, diethylene glycol monovinyl ether was added at the end of metathesis reactions; diethylene glycol monovinyl ether not only can quench the CM reaction, but the glycol tail makes the catalyst water-soluble so that it can be easily removed by washing the product with water. The addition of diethylene glycol monovinyl ether did not mitigate the solubility issue, showing that CM was not the cause of the insolubility. The present inventors then turned their attention to two other possible undesired reactions of the CM products, Michael reaction or free radical polymerization. The inventors thought that Michael addition to the $\alpha,\beta$ unsaturated carboxylic acid groups was less likely, due to the absence of strong base catalyst, and the relatively low reactivity of the possible Michael donors (—OH or methylene groups). The inventors therefore examined whether the crosslinking was caused by a free radical mechanism. Experiments were carried out in which 3,5-di-tert-4-butylhydroxytoluene (BHT), a commonly used antioxidant capable of scavenging free radicals, was added before the reaction. As BHT is not soluble in water, the majority of it would remain in the polymer upon addition of the reaction mixture to water to precipitate the product. The presence of BHT would be expected to suppress the generation of free radicals during reaction, isolation, and product storage. Indeed, the BHT containing products remained soluble after two months storage at room temperature. Furthermore, dissolution of these products in THF and precipitation in hexane afforded products that were still readily soluble in THF. Prevention of crosslinking by BHT addition strongly supports the notion that the cross-linking and solubility loss was caused by a free radical mechanism, while providing a useful means to avoid the problem.

To further confirm this hypothesis, alkaline hydrolysis of the ester groups of metathesis products was performed according to a previously reported method (Freire, C. S. R.; Silvestre, A. J. D.; Pascoal Neto, C.; Rocha, R. M. A., An Efficient Method for Determination of the Degree of Substitution of Cellulose Esters of Long Chain Aliphatic Acids. Cellulose 2005, 12, (5), 449-458). After acidification, long chain acids were extracted into $CH_2Cl_2$, and then the $CH_2Cl_2$ extract was washed extensively by water. A suitable amount of BHT was added to prevent coupling during this process. $^1H$ NMR was performed on the acid products collected from samples with and without solubility problems. While samples without solubility problems afforded an ester product with a spectrum identical with undec-2-enedioic acid, those with solubility problems afforded acids with an extra peak at 0.79 ppm in the proton spectrum, indicating the occurrence of dimerization (FIGS. 5A and 5B).

The synthesis of long chain $\alpha,\beta$ unsaturated carbonyl derivatives via olefin metathesis has been the topic of several studies (Rybak, A.; Meier, M. A. R., Cross-metathesis of Fatty Acid Derivatives with Methyl Acrylate: Renewable Raw Materials for the Chemical Industry. Green Chem. 2007, 9, (12), 1356-1361; and Djigoue, G. B.; Meier, M. A. R., Improving the Selectivity for the Synthesis of Two Renewable Platform Chemicals via Olefin Metathesis. Appl. Catal. A-Gen. 2009, 368, (1-2), 158-162; and Zerkowski, J. A.; Solaiman, D. K. Y., Omega-Functionalized Fatty Acids, Alcohols, and Ethers via Olefin Metathesis. J. Am. Oil Chem. Soc. 2012, 89, (7), 1325-1332). Recently, de Espinosa et al. reported side-chain modification of poly(2-oxazoline) employing 10-undecenoyl as the side chain, via crossmetathesis with acrylates (de Espinosa, L. M.; Kempe, K.; Schubert, U. S.; Hoogenboom, R.; Meier, M. A. R., Side-Chain Modification and "Grafting Onto" via Olefin Cross-Metathesis. Macrom. Rapid Comm. 2012, 33, (23), 2023-2028). However, none of these studies have mentioned the crosslinking problem that the inventors report herein. The inventors' results may provide a way to understand and avoid such crosslinking, while retaining the possibility that the double bond can be preserved should it be desirable to do so.

Compounds and methods described in this specification may be useful for structure-property studies, particularly those aimed at developing polymers for drug delivery. Particular applications for the compounds and methods in the area of drug delivery can include, controlled-release drug delivery systems (delivery of compounds in response to stimuli, such as pH, or time), controlled-release coatings, increasing bioavailability of drugs, and maintaining drug supersaturation in the GI tract. Other biomedical applications include targeted delivery systems (by appending sensitive targeting moieties using the gentle cross metathesis chemistry taught herein), prodrugs (appending the drug via metathesis chemistry with a moiety that links to the drug through a hydrolysable linker), or hydrogels (appending moieties capable of physical or chemical crosslinking upon exposure to a trigger). Other applications include water-dispersible coatings additives, adhesives, surfactants, self-plasticized plastics, sensors, and an extremely wide array of other potential applications.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties including patents, published patent applications, and non-patent literature, and as such are intended to provide an efficient way of supplementing the enabling disclosure of this invention as well as provide background detailing the level of ordinary skill in the art.

The invention claimed is:

1. A method for the synthesis of a cross-metathesized polysaccharide derivative, the method comprising:
providing an olefin-substituted polysaccharide which has one or more olefin-terminated side chains;
providing a solvent capable of dissolving the olefin-substituted polysaccharide;
providing a cross-metathesis partner at a cross-metathesis partner: terminal olefin ratio exceeding 1:1;
providing Hoveyda-Grubbs $2^{nd}$ Generation Catalyst; and
reacting the cross-metathesis partner and the olefin-substituted polysaccharide in the solvent for a time and under conditions sufficient to obtain a cross-metathesized polysaccharide derivative;
wherein the cross-metathesized polysaccharide derivative is a cellulose ω-carboxyester comprising:

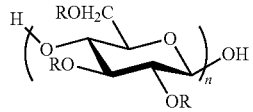

wherein:
R is H or $COCH_3$ or $COCH_2CH_3$ or $CO(CH_2)_2CH_3$ or R';
at least one R must be R';

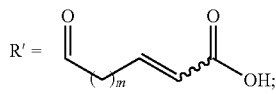

and
m=1-20 and n=10-10,000.

2. The method of claim 1, wherein the cross-metathesis partner is an acrylic acid, an acrylate ester, or an acrylamide.

3. The method of claim 1, wherein the olefin-substituted polysaccharide is a linear or branched polysaccharide or oligosaccharide comprising monosaccharide, disaccharide, or trisaccharide repeating monomer units.

4. The method of claim 1, wherein the providing of the olefin-substituted polysaccharide comprises synthesizing the olefin-substituted polysaccharide from a cellulose ester.

5. The method of claim 4, wherein the olefin-substituted polysaccharide is a cellulose alkanoate undec-10-enoate.

6. The method of claim 5, wherein the olefin-substituted polysaccharide is a cellulose undec-10-enoate derivative, cellulose pent-4-enoate, or cellulose acrylate derivative.

7. The method of claim 6, wherein the olefin-substituted polysaccharide is a cellulose undec-10-enoate derivative comprising:

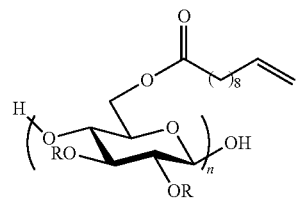

wherein R is H or $COCH_3$ or $COCH_2CH_3$ or $CO(CH_2)_2CH_3$ or R'; and
at least one R must be R';

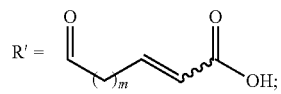

and
m=1-20 and n=10-10,000.

8. The method of claim 6, wherein the cellulose undec-10-enoate derivative is cellulose acetate undec-10-enoate, cellulose acetate propionate undec-10-enoate, cellulose acetate butyrate undec-10-enoate, or cellulose acetate adipate undec-10-enoate.

9. The method of claim 1, wherein the solvent is one or more of acetone, ethyl acetate, dimethyl sulfoxide, dimethylformamide, DMAc, DMI, or isopropyl alcohol.

10. The method of claim 1, wherein the cross-metathesis partner: terminal olefin ratio exceeds 20:1.

11. The method of claim 1, further comprising providing a free radical scavenger.

12. The method of claim 11, wherein the free radical scavenger is butylated hydroxytoluene or butylated hydroxyanisole.

13. The method of claim 1, wherein the one or more olefin-terminated side chains are substituted.

14. The method of claim 1, wherein the one or more olefin-terminated side chains have one or more functional groups chosen from hydroxyl, carboxyl, carbonyl, amine, amide, aldehyde, carboxylate, ester, ether, nitrate, nitroso, sulfide, and sulfhydryl.

15. The method of claim 1, wherein the one or more olefin-terminated side chains include at least one heteroatom chosen from phosphorus, sulfur, oxygen, nitrogen, boron, chlorine, bromine, iodine, and fluorine.

16. A method for the synthesis of a cellulose ω-carboxyester, comprising:
the reaction:

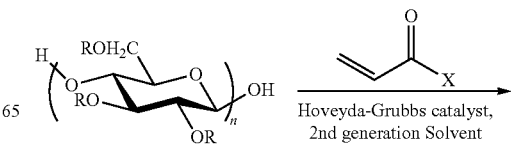

-continued

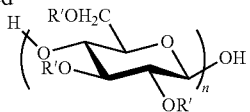

wherein:
R is H or COCH$_3$ or COCH$_2$CH$_3$ or CO(CH$_2$)$_2$CH$_3$ or CO(CH$_2$)$_m$CH=CH$_2$;
at least one R group must be CO(CH$_2$)$_m$CH=CH$_2$;
R' is H or COCH$_3$ or COCH$_2$CH$_3$ or CO(CH$_2$)$_2$CH$_3$ or CO(CH$_2$)$_m$CH=CHCO$_2$H;
at least one R' must be CO(CH$_2$)$_m$CH=CHCO$_2$H;
m=1-20 and n=10-10,000; and
x=chlorine atom.

17. A cross-metathesized polysaccharide derivative, which is a cellulose ω-carboxyester comprising:

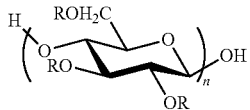

wherein:
R is H or COCH$_3$ or COCH$_2$CH$_3$ or CO(CH$_2$)$_2$CH$_3$ or R':
at least one R must be R';

and

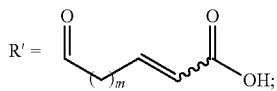

m=1-20 and n=10-10,000.

18. The cellulose ω-carboxyester of claim 17, which is a cellulose acetate monododec-10-endioate (CADod), a cellulose acetate butyrate monododec-2-endioate (CABDod), or a cellulose acetate propionate monododec-2-endioate (CAPDod).

19. The cellulose ω-carboxyester of claim 17, which is a cellulose acetate monododec-10-endioate (CADod067) having 0.67 substituents per monosaccharide unit, a cellulose acetate monododec-10-endioate (CADod128) having 1.28 substituents per monosaccharide unit, a cellulose acetate butyrate monododec-2-endioate (CABDod036) having 0.36 substituents per monosaccharide unit, or a cellulose acetate butyrate monododec-2-endioate (CABDod051) having 0.51 substituents per monosaccharide unit.

20. A pharmaceutical composition comprising an active pharmaceutical ingredient and a cellulose ω-carboxyester of claim 19.

* * * * *